(12) United States Patent
Morimoto et al.

(10) Patent No.: US 11,103,220 B2
(45) Date of Patent: Aug. 31, 2021

(54) ULTRASONIC ENDOSCOPE

(71) Applicant: FUJIFILM Corporation, Tokyo (JP)

(72) Inventors: Yasuhiko Morimoto, Ashigara-kami-gun (JP); Katsuya Yamamoto, Ashigara-kami-gun (JP); Satoru Okada, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 392 days.

(21) Appl. No.: 16/227,863

(22) Filed: Dec. 20, 2018

(65) Prior Publication Data

US 2019/0117200 A1    Apr. 25, 2019

Related U.S. Application Data

(63) Continuation of application No. PCT/JP2017/015340, filed on Apr. 14, 2017.

(30) Foreign Application Priority Data

Jun. 30, 2016    (JP) .............................. JP2016-129865

(51) Int. Cl.
*A61B 8/12*    (2006.01)
*A61B 8/00*    (2006.01)
(Continued)

(52) U.S. Cl.
CPC .............. *A61B 8/546* (2013.01); *A61B 1/273* (2013.01); *A61B 8/12* (2013.01); *A61B 8/445* (2013.01);
(Continued)

(58) Field of Classification Search
CPC ........... A61B 8/12; A61B 8/44; A61B 8/4444; A61B 8/445; A61B 8/4483; A61B 8/4488; A61B 8/546; B06B 1/0622
See application file for complete search history.

(56) References Cited

U.S. PATENT DOCUMENTS

2006/0234788 A1* 10/2006 Chuang ............... H04M 1/0202
                                                                    455/575.7
2008/0009742 A1    1/2008 Kondoh
(Continued)

FOREIGN PATENT DOCUMENTS

CN    101396289 A    4/2009
CN    101612050 A    12/2009
(Continued)

OTHER PUBLICATIONS

International Preliminary Report on Patentability and Written Opinion of the International Searching Authority (Forms PCT/IB/326, PCT/IB/373, and PCT/ISA/237) for International Application No. PCT/JP2017/015340, dated Jan. 10, 2019, with an English translation.

(Continued)

*Primary Examiner* — Mark D Remaly
(74) *Attorney, Agent, or Firm* — Birch, Stewart, Kolasch & Birch, LLP

(57) ABSTRACT

An ultrasonic endoscope includes a plurality of ultrasonic vibrators; a distal end part that houses the plurality of ultrasonic vibrators; an electrically conductive endoscopic structure housed in or connected to the distal end part; a thermally conductive member connected to the plurality of ultrasonic vibrators; and an electrically insulating thermally conductive member connected to the endoscopic structure. The thermally conductive member and the electrically insulating thermally conductive member are connected to each other. Thus, the ultrasonic endoscope that has a heat release structure which transmits the heat generated from the ultrasonic vibrators to the electrically conductive endoscopic structure housed in the distal end part and which can efficiently release the heat therefrom while electric safety is secured; and that can prevent a burn of an alimentary canal (Continued)

by suppressing a temperature rise of surfaces of the ultrasonic vibrators is provided.

20 Claims, 18 Drawing Sheets

(51) Int. Cl.
*B06B 1/06* (2006.01)
*A61B 1/273* (2006.01)
(52) U.S. Cl.
CPC .......... *A61B 8/4444* (2013.01); *B06B 1/0622* (2013.01); *A61B 8/4483* (2013.01)

(56) References Cited

U.S. PATENT DOCUMENTS

| | | |
|---|---|---|
| 2008/0300492 A1 | 12/2008 | Nagano et al. |
| 2008/0306389 A1 | 12/2008 | Nagano et al. |
| 2009/0088646 A1 | 4/2009 | Nagano et al. |
| 2009/0088647 A1 | 4/2009 | Nagano et al. |
| 2009/0234233 A1 | 9/2009 | Nagano et al. |
| 2009/0318831 A1 | 12/2009 | Aoki et al. |

FOREIGN PATENT DOCUMENTS

| | | |
|---|---|---|
| EP | 2671514 A1 | 12/2013 |
| JP | 61-73639 A | 4/1986 |
| JP | 2008-22077 A | 1/2008 |
| JP | 2008/295749 A | 12/2008 |
| JP | 2008-301893 A | 12/2008 |
| JP | 2009/240755 A | 10/2009 |
| JP | 5329065 B2 | 10/2013 |

OTHER PUBLICATIONS

International Search Report (Form PCT/ISA/210) for International Application No. PCT/JP2017/015340, dated Jun. 20, 2017, with English translation.
Extended European Search Report dated Apr. 18, 2019 for corresponding European Appication No. 17819609.3.
Chinese Office Action dated Dec. 25, 2020 for corresponding Chinese Patent Application No. 201780038895.X with partial English translation.

\* cited by examiner

ULTRASONIC ENDOSCOPE

CROSS-REFERENCE TO RELATED APPLICATIONS

This application is a Continuation of PCT International Application No. PCT/JP2017/015340 filed on Apr. 14, 2017, which claims priority under 35 U.S.C. § 119(a) to Japanese Patent Application No. 2016-129865 filed on Jun. 30, 2016. The above application is hereby expressly incorporated by reference, in its entirety, into the present application.

BACKGROUND OF THE INVENTION

1. Field of the Invention

The present invention relates to ultrasonic endoscopes, and more particularly relates to an ultrasonic endoscope having, at a distal end part thereof, a heat release structure for releasing the heat generated from very small ultrasonic vibrators used in the ultrasonic endoscope that is inserted into a body cavity.

2. Description of the Related Art

An ultrasound diagnostic apparatus using ultrasonic imaging typically includes an ultrasound probe for body surface that is used by being brought into contact with a subject, and an ultrasound probe for body cavity that is used by being inserted into a body cavity of a subject. Furthermore, in recent years, an ultrasonic endoscope is used which is a combination of an endoscope for optically observing the inside of a subject, and an ultrasound probe for body cavity.

When an ultrasound probe transmits an ultrasound beam to a subject such as a human body and receives an ultrasound echo generated from the subject, ultrasound image information is acquired.

Based on the ultrasound image information, an ultrasound image of an object existing in the subject (for example, an internal organ or a lesion tissue) is displayed on a display unit of an ultrasonic endoscope apparatus body that is connected to the ultrasonic endoscope.

A typically used example of ultrasonic transducers (ultrasonic vibrator array) that transmit and receive ultrasonic waves is a plurality of ultrasonic vibrators (piezoelectric vibrators) in which electrodes are formed on both surfaces of a material (piezoelectric body) that exhibits a piezoelectric effect.

When a voltage is applied to the electrodes of the ultrasonic vibrators, the piezoelectric body is expanded and contracted by the piezoelectric effect and ultrasonic waves are generated. The plurality of ultrasonic vibrators are arranged in a one-dimensional form or a two-dimensional form to serve as an ultrasonic vibrator array, and by successively driving the plurality of ultrasonic vibrators, an ultrasound beam that is transmitted in a desirable direction can be formed.

Also, the ultrasonic vibrators are expanded and contracted by receiving propagating ultrasonic waves, and generate electric signals. The electric signals are used as detection signals of ultrasonic waves.

The ultrasonic endoscope including the plurality of ultrasonic vibrators is provided with an ultrasonic observation portion at a distal end part of the endoscope, as a major purpose, to observe the gallbladder or pancreas via an alimentary canal. The distal end part of the ultrasonic endoscope is provided with, in addition to the ultrasonic observation portion, an optical sensor, a light, an air supply port, a water supply port, and a suction port, like a typical endoscope not provided with the ultrasonic observation portion. With such an ultrasonic endoscope that is inserted into a body cavity of a subject, in particular, an upper alimentary canal or a bronchus, it is requested to decrease the diameter of an insertion section of the ultrasonic endoscope, and the size of the distal end part, in particular, the size of the ultrasonic observation portion, to reduce the physical burden of the subject.

Also, the distal end part of the ultrasonic endoscope involves heat generating factors, such as the ultrasonic vibrators and the light source of the endoscope. The insertion section of the ultrasonic endoscope, in particular, the distal end part directly contacts the inside of a living body such as a human body. Hence, for safety reasons such as preventing a moderate-temperature burn, it is demanded to set the surface temperature of the insertion section to a predetermined temperature or lower.

Owing to this, an ultrasonic endoscope that has means for decreasing the surface temperature of the distal end part while the size of the distal end part is held small is requested. In recent years, various suggestions are made for cooling the distal end part of the ultrasonic endoscope that is a heat generation source (see JP5329065B, JP2009-240755A, and JP2008-22077A).

JP5329065B discloses an ultrasonic endoscope including an insertion section having a bending part. The insertion section has a backing material having a front surface on which a plurality of ultrasonic transducers are disposed, an exterior member made of stainless steel (SUS) or the like that houses the plurality of ultrasonic transducers at a distal end of the insertion section, and a thermally conductive member that is disposed in the exterior member and that contacts a back surface of the backing material and an inner surface of the exterior member. With this configuration, the heat generated from the ultrasonic transducers and transmitted to the backing material, and the heat generated from the backing material as the result that the backing material receives ultrasonic waves from the ultrasonic transducers are transmitted to the thermally conductive member via the backing material, are further transmitted to the exterior member via the thermally conductive member, and are released from the exterior member to the outside of the ultrasonic endoscope. Thus, with JP5329065B, the heat release from the ultrasonic transducers to the outside is promoted.

JP2009-240755A discloses an ultrasonic endoscope in which a signal line housing part that is located below a backing material supporting a plurality of ultrasonic transducers and that houses a plurality of signal lines (shield line group) is filled with a highly thermally conductive filling material; and a highly thermally conductive layer such as a copper foil is disposed on a bottom surface, side surfaces, and a rear surface of the signal line housing part. The heat generated from the ultrasonic transducers is efficiently released by diffusing the heat to a surface of an exterior material via a backing layer, the highly thermally conductive filling material in the signal line housing part, and the highly thermally conductive layer.

JP2008-22077A discloses an ultrasound probe in which individual metal thin plates, serving as thermally conductive materials, are provided on earth electrode sides of a plurality of piezoelectric elements. The individual metal thin plates are thermally connected to a heat release base that is located below a backing material that supports the piezoelectric elements, via a common metal thin plate or an electrically insulating thermally conductive material that is joined to an end surface of the backing material. The heat generated from the piezoelectric elements is released to the heat release base via the individual metal thin plates, and the common metal thin plate, or the electrically insulating thermally conductive member.

SUMMARY OF THE INVENTION

With the ultrasonic endoscope disclosed in JP5329065B, only a heat release path for releasing the heat generated from the ultrasonic vibrators and the backing material layer to the exterior member via the thermally conductive member is taken into account, and hence it is difficult to further improve the heat release effect. Further, with the technology disclosed in JP5329065B, heat does not stay in the ultrasonic vibrators and the backing material layer; however, since the heat is released to the exterior member of, for example, SUS, the heat may be released to the inside of the body cavity near the distal end part of the ultrasonic endoscope. In this case, a temperature rise is suppressed by a certain degree because the heat is diffused from the exterior member; however, this may involve a problem of an increase in temperature of the exterior member of the distal end part of the ultrasonic endoscope and an increase in temperature in the periphery of the distal end part.

Also, with the ultrasonic endoscope or the like disclosed in JP2009-240755A, a high-frequency treatment tool is used, and hence a distal end main body case (exterior body) uses an electrically insulating resin. To allow washing, disinfection, and sterilization of the endoscope, the distal end main body case is required to be chemical resistant, and typically uses polysulfone, polyphenylsulfone, or polyetherimide. Owing to this, the distal end main body case has low thermal conductivity, and even through a member with high thermal conductivity is bonded to the electrically insulating resin, heat is not efficiently released.

Also, with the technologies disclosed in JP2009-240755A and JP2008-22077A, since heat is finally released by diffusing the heat to the exterior body, the surface temperature of the exterior body may rise, like the technology disclosed in JP5329065B.

Note that, since the technology disclosed in JP2008-22077A is used for a body surface of a subject, even when heat is diffused and released to the exterior body, the heat can be efficiently released to the outside of the body. However, if the technology disclosed in JP2008-22077A is applied to the ultrasonic endoscope that is used in a body cavity of a subject, this may increase the surface temperature of the exterior body. Therefore, it is difficult to satisfy the demand that the surface temperature of the insertion section is set to the predetermined temperature or lower.

Presently, in order to improve diagnostic accuracy of an ultrasonic endoscope, the transmission output of ultrasonic waves is increased by laminating ultrasonic transducers (vibrators), and reception sensitivity is increased by increasing the number of ultrasonic vibrators.

As the result, the amount of heat released from the ultrasonic vibrators is increased, and due to the heat generated from the ultrasonic vibrators, the temperature of the insertion section that contacts a body cavity wall, in particular, the temperature of the distal end part at which the ultrasonic vibrators are disposed may be increased.

Further, with the ultrasonic endoscope, to improve diagnostic accuracy by improving image quality or the like of an ultrasound image to be obtained, the driving voltage for driving the ultrasonic vibrators may be increased, in addition to increasing the reception sensitivity. However, with such an ultrasonic endoscope, the heat generated from the ultrasonic vibrators (ultrasonic transducers) due to the increase in the driving voltage may cause a further temperature rise.

As described above, to improve the diagnostic accuracy by improving the image quality or the like of the ultrasound image, when the number of the ultrasonic vibrators is increased, when the driving voltage of the ultrasonic vibrators is increased, or when the transmission output of ultrasonic waves is increased, the technologies disclosed in JP5329065B, JP2009-240755A, and JP2008-22077A involve problems. The problems are possibly increasing the ambient temperatures, such as the ambient temperature of the distal end part of the ultrasonic endoscope that directly contacts the inside of a living body such as a human body, and the ambient temperature of the exterior member, to allowable temperatures or higher.

It is required to suppress heat generation and a temperature rise while the diameter of the insertion section and the size of the distal end part are held small, and a significant issue is how the heat generated from the ultrasonic vibrators is released.

Here, a metal endoscopic structure in an ultrasonic endoscope has large thermal capacity and high thermal conductivity, and hence by releasing the heat generated from ultrasonic vibrators to the metal endoscopic structure via a thermally conductive member such as a copper foil, the heat can be released to the proximal end side of the endoscope. However, since a voltage in a range from 10 V to 100 V is applied to the driving signal for driving the ultrasonic vibrators, the ultrasonic vibrator structure including the copper foil is required to be electrically insulated from the endoscopic structure. Thus, it is difficult to release the heat transmitted to the copper foil with high thermal conductivity, to the endoscopic structure.

The present invention addresses the above-described problems of related art, and it is an object of the present invention to provide an ultrasonic endoscope that has a heat release structure that transmits the heat generated from ultrasonic vibrators to, for example, an electrically conductive endoscopic structure which is housed in a distal end part and which can efficiently release the heat from the electrically conductive endoscopic structure, while the diameter of an insertion section is held small, the size of the distal end part is held small, and electric safety is secured; that can prevent a burn of an alimentary canal by suppressing a temperature rise of surface of the ultrasonic vibrators; and as a result, that can improve diagnostic accuracy in ultrasonic diagnosis.

To attain the above-described object, an ultrasonic endoscope according to a first aspect of the present invention includes a plurality of ultrasonic vibrators; a distal end part that houses the plurality of ultrasonic vibrators; an electrically conductive endoscopic structure housed in or connected to the distal end part; a thermally conductive member connected to the plurality of ultrasonic vibrators; and an electrically insulating thermally conductive member connected to the endoscopic structure. The thermally conductive member and the electrically insulating thermally conductive member are connected to each other.

Preferably, the thermally conductive member is an electrically/thermally conductive member, and the endoscopic structure is made of metal.

Preferably, the thermally conductive member has a first thermally conductive member that is directly connected to the plurality of ultrasonic vibrators, and a second thermally conductive member that connects the first thermally conductive member and the electrically insulating thermally conductive member to each other.

Preferably, the electrically insulating thermally conductive member is removably connected to the thermally conductive member or the endoscopic structure.

Preferably, the thermally conductive member has an exposed portion exposed to the endoscopic structure, and the exposed portion is covered with an electrically insulating coating member.

Preferably, the electrically insulating thermally conductive member has a withstand voltage of 1.5 kV or higher.

Preferably, the electrically insulating thermally conductive member has a thickness of 3 mm or smaller.

Preferably, the electrically insulating thermally conductive member has a thermal conductivity of 0.5 W/mK or higher.

Preferably, the endoscopic structure is an erecting base component, a forceps pipe line component, or a distal-end-side ring component of an angle sub-assembly.

Preferably, at least one of the erecting base component or the forceps pipe line component is disposed on a proximal end side of the ultrasonic endoscope with respect to the plurality of ultrasonic vibrators.

Preferably, the thermally conductive member has a thermal conductivity of 0.5 W/mK or higher.

Preferably, the ultrasonic endoscope further includes a plurality of ultrasonic cables individually connected to the plurality of ultrasonic vibrators; and a cable insertion hole that are provided in the distal end part and through which the plurality of ultrasonic cables are inserted. Preferably, the thermally conductive member is partly disposed in the cable insertion hole.

Preferably, the thermally conductive member has a first thermally conductive member that is directly connected to the plurality of ultrasonic vibrators, and a second thermally conductive member that connects the first thermally conductive member and the electrically insulating thermally conductive member to each other. Preferably, the second thermally conductive member is disposed in the cable insertion hole.

Preferably, the electrically insulating thermally conductive member is a wall of the cable insertion hole that contacts an electrically conductive structural body of the endoscopic structure, and the wall has a thickness of 3 mm or smaller.

Preferably, the electrically insulating thermally conductive member is a thermally conductive ceramic screw that attaches the thermally conductive member to an electrically conductive structural body of the endoscopic structure, and a distal end portion of the screw contacts the electrically conductive structural body.

Preferably, the distal end part has an electrically insulating exterior member, and the endoscopic structure is housed in or connected to the exterior member.

Preferably, the plurality of ultrasonic vibrators are convex type or radial type.

To attain the above-described object, an ultrasonic endoscope according to a second aspect of the present invention includes a plurality of ultrasonic vibrators; and a distal end part that houses the plurality of ultrasonic vibrators. The distal end part has an ultrasonic vibrator array in which the plurality of ultrasonic vibrators are arranged; a distal end case that is provided on a distal end side of the ultrasonic endoscope and that houses the ultrasonic vibrator array; a cable insertion hole that is provided in the distal end case, and through which a plurality of cables are inserted, the plurality of cables being individually electrically connected to the plurality of ultrasonic vibrators of the ultrasonic vibrator array; an electrically conductive endoscopic structure housed in or connected to the distal end case on a proximal end side of the ultrasonic endoscope; an electrically/thermally conductive member that is connected to the ultrasonic vibrator array and that releases heat generated from the plurality of ultrasonic vibrators; and an electrically insulating thermally conductive member disposed in contact with the electrically conductive endoscopic structure. The electrically/thermally conductive member is extended to the proximal end side of the ultrasonic endoscope. A proximal end side of the extended electrically/thermally conductive member is connected to the electrically insulating thermally conductive member.

To attain the above-described object, an ultrasonic endoscope according to a third aspect of the present invention includes a plurality of ultrasonic vibrators; and a distal end part that houses the plurality of ultrasonic vibrators. The distal end part has an ultrasonic vibrator array in which the plurality of ultrasonic vibrators are arranged; a distal end case that is provided on a distal end side of the ultrasonic endoscope and that houses the ultrasonic vibrator array; a cable insertion hole that is provided in the distal end case, and through which a plurality of cables are inserted, the plurality of cables being individually electrically connected to the plurality of ultrasonic vibrators of the ultrasonic vibrator array; an electrically conductive endoscopic structure housed in or connected to the distal end case on a proximal end side of the ultrasonic endoscope; an electrically conductive first thermally conductive member that is connected to the ultrasonic vibrator array and that releases heat generated from the plurality of ultrasonic vibrators; an electrically insulating thermally conductive member disposed in contact with the electrically conductive endoscopic structure; and an electrically conductive second thermally conductive member whose distal end side is connected to the first thermally conductive member, that is disposed to extend in the distal end case to the proximal end side of the ultrasonic endoscope, and whose proximal end side is connected to the electrically insulating thermally conductive member.

With the present invention, the ultrasonic endoscope can be provided that has a heat release structure that transmits the heat generated from the ultrasonic vibrators to, for example, the electrically conductive endoscopic structure which is housed in the distal end part and which can efficiently release the heat from the electrically conductive endoscopic structure, while the diameter of the insertion section is held small, the size of the distal end part is held small, and electric safety is secured; that can prevent a burn of an alimentary canal by suppressing a temperature rise of surfaces of the ultrasonic vibrators; and as a result, that can improve diagnostic accuracy in ultrasonic diagnosis.

DESCRIPTION OF THE PREFERRED EMBODIMENTS

An ultrasonic endoscope according to the present invention is described below in detail based on preferred embodiments shown in the accompanying drawings.

First Embodiment

Figure 1:
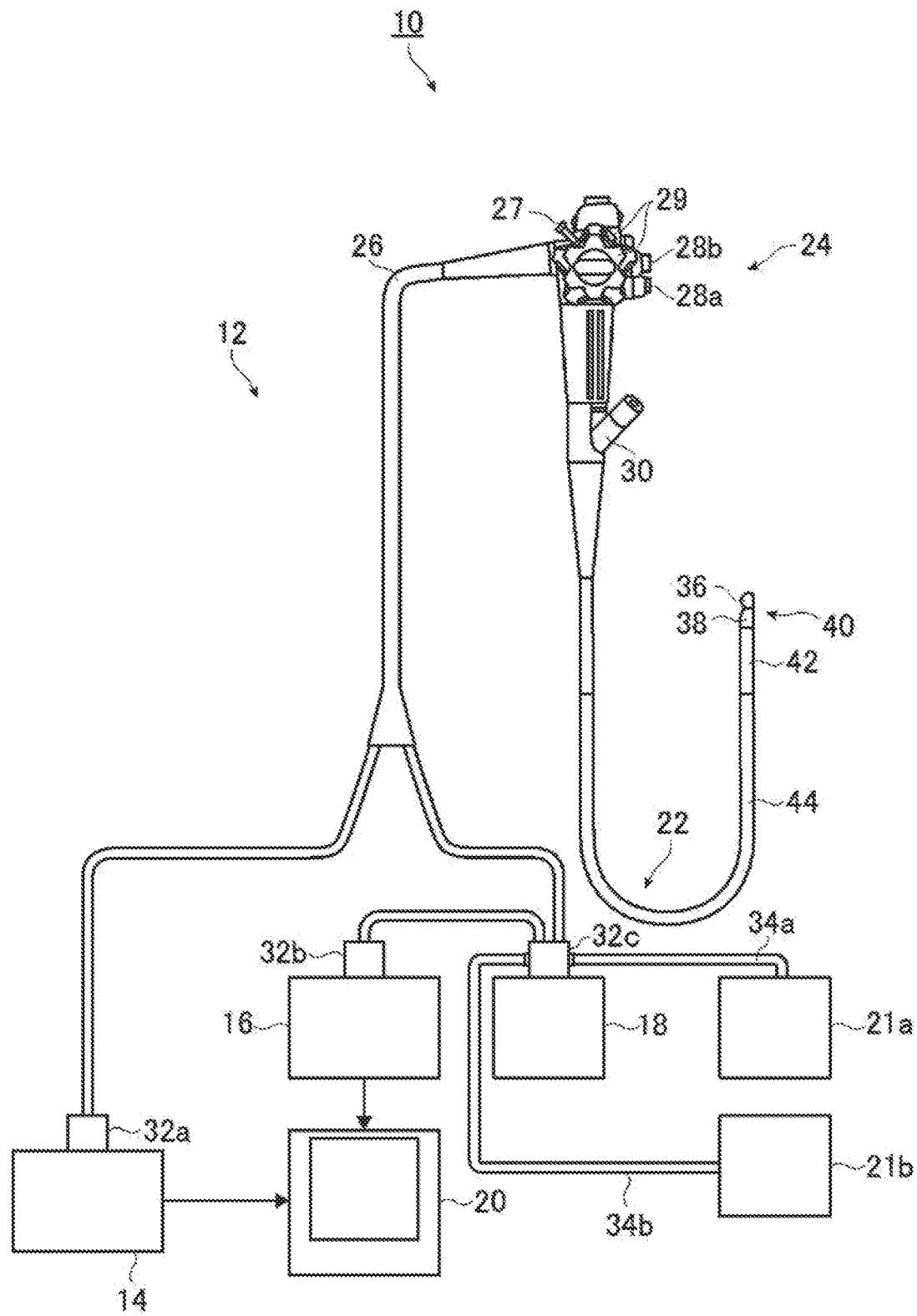
FIG. 1 is a schematic configuration diagram showing an example of a configuration of an ultrasonic inspection system that uses an ultrasonic endoscope according to an embodiment of the present invention.
Figure 2:
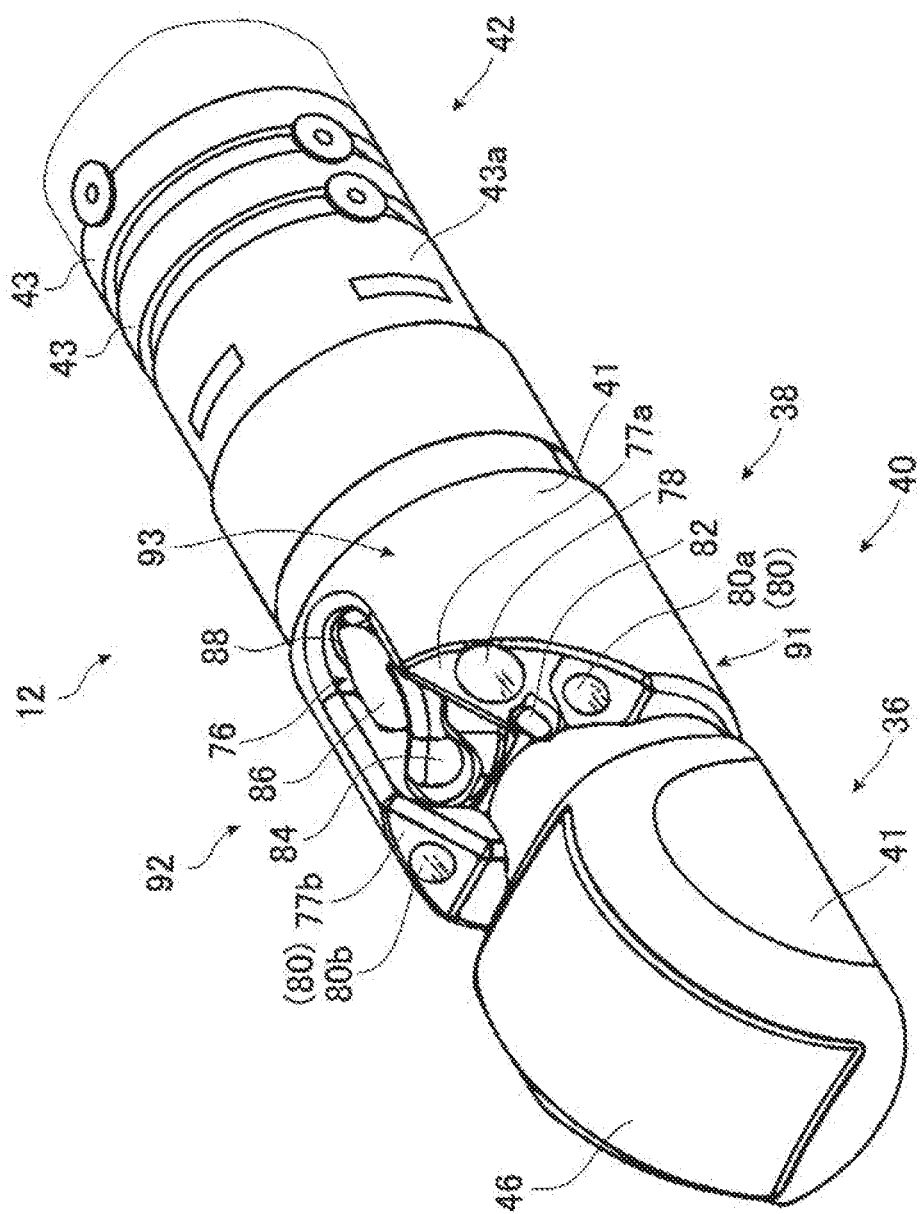
FIG. 2 is a partial enlarged perspective view showing configurations of a distal end part and a bending part of the ultrasonic endoscope shown in FIG. 1.
Figure 3:
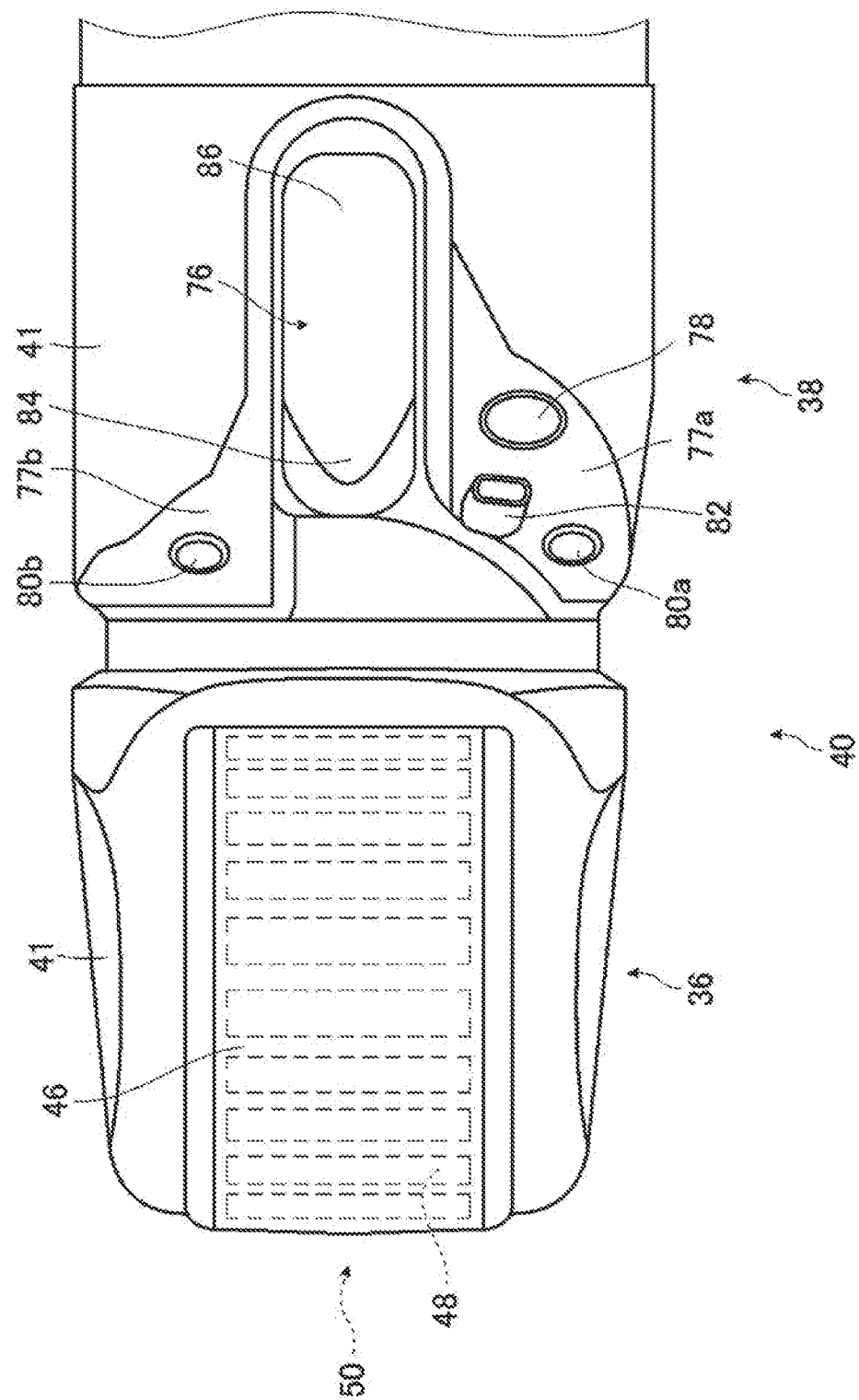
FIG. 3 is a partial enlarged plan view showing the distal end part of the ultrasonic endoscope shown in FIG. 1.

FIG. 1 is a schematic configuration diagram showing an example of a configuration of an ultrasonic inspection system that uses an ultrasonic endoscope according to a first embodiment of the present invention. FIG. 2 is a partial enlarged perspective view showing configurations of a distal end part and a bending part of the ultrasonic endoscope shown in FIG. 1. FIG. 3 is a partial enlarged plan view showing the distal end part and its periphery of the ultrasonic endoscope shown in FIG. 1.

An ultrasonic inspection system 10 shown in FIG. 1 enables the gallbladder or the pancreas, which is difficult to be observed by an ultrasonic inspection from a body surface of a subject such as a patient, to be observed through an alimentary canal, such as the esophagus, stomach, duodenum, small intestine, large intestine, or the like, which is a body cavity of the subject. The ultrasonic inspection system 10 inserts an ultrasonic endoscope according to the present invention having an ultrasonic observation portion that includes a plurality of ultrasonic vibrators and that acquires an ultrasonic tomographic image (hereinafter referred to as ultrasound image), and an endoscopic observation portion that acquires an endoscope optical image (hereinafter referred to as endoscope image), into a body cavity of a subject; and acquires an ultrasound image of an observation target region of the subject while observing an endoscope image of the subject.

Also, in the ultrasonic endoscope of the present invention, a thermally conductive member, such as a copper foil or the like that gives roles of a shield and a heat release effect to side surfaces of the plurality of ultrasonic vibrators that generate heat during an ultrasonic inspection, for example, an electrically/thermally conductive member is disposed. The heat transmitted from the ultrasonic vibrators to the thermally conductive member such as the copper foil is efficiently released, an increase in heat of the surfaces of the ultrasonic vibrators is suppressed, and hence a thermal burn of an alimentary canal can be prevented from occurring.

Thus, according to the present invention, for example, a copper foil, or an electrically conductive member having high thermal conductivity and connected to a copper foil, that is, an electrically/thermally conductive member is disposed in an exterior member (distal end case) of a distal end main body, preferably, at a position as close as possible to an endoscopic structure having high thermal conductivity and disposed in an electrically insulating exterior member, for example, a metal endoscopic structure. With this configuration, the heat is transmitted from the plurality of ultrasonic vibrators to the endoscopic structure via the electrically/thermally conductive member, such as the copper foil, and is released from the endoscopic structure. At this time, according to the present invention, to further secure electric safety, an electrically insulating thermally conductive member is disposed between the metal endoscopic structure and the thermally conductive member such as a copper foil, and a thermally conductive electrically insulating layer is provided between the thermally conductive member such as the copper foil and the metal endoscopic structure. Accordingly, the heat is transmitted to the endoscopic structure while electric insulation is secured.

That is, according to the present invention, the destination to which the heat of the plurality of ultrasonic vibrators is released is not the exterior member, but the endoscopic structure that is housed in or connected to the exterior member. Thus, the exterior member is only required to have electrically insulating properties, does not have to have high thermal conductivity, and may be made of a known resin material conventionally used for an ultrasonic endoscope, for example, polysulfone, polyphenylsulfone, or polyetherimide which is disclosed in JP2009-240755A and having low thermal conductivity.

According to the present invention, the exterior member is only required to have electrically insulating properties because if the exterior member does not have electrically insulating properties and is electrically conductive, heat is transmitted to a subject such as a human body and a burn such as a moderate-temperature burn may occur. Also, since a high driving voltage is applied to the ultrasonic vibrators, if electric current leaks to an electrically conductive exterior member, the electric current may also possibly leak to a human body.

As shown in FIG. 1, the ultrasonic inspection system 10 includes an ultrasonic endoscope 12 according to the first embodiment of the present invention having a heat release structure at a distal end part thereof, an ultrasonic processor device 14 that generates an ultrasound image, an endoscopic processor device 16 that generates an endoscope image, a light source device 18 that supplies illumination light that illuminates a body cavity to the ultrasonic endoscope 12, and a monitor 20 that displays the ultrasound image and/or the endoscope image.

The ultrasonic inspection system 10 further includes a water supply tank 21a that stores washing water or the like, and a suction pump 21b that sucks an object to be sucked in the body cavity (including supplied washing water and so forth). Although not shown, the ultrasonic inspection system 10 may further include a supply pump or the like that supplies washing water in the water supply tank 21a or gas such as the outside air to a pipe line (not shown) in the ultrasonic endoscope 12.

First, as shown in FIGS. 1 to 3, the ultrasonic endoscope 12 according to the present invention has an ultrasonic observation portion 36 including a heat release structure (70: see FIGS. 5 to 6) being a feature of the present invention, and an endoscopic observation portion 38 at a distal end part 40, image captures the inside of a body cavity of a subject, and acquires an ultrasound image (echo signal) and an endoscope image (image signal).

The ultrasonic endoscope 12 is composed of an insertion section 22 that includes the ultrasonic observation portion 36 and the endoscopic observation portion 38 at the distal end part, and that is inserted into the body cavity of the subject; an operation section 24 that is connected to a proximal end part of the insertion section 22 and with which an operator, such as a doctor or a technician, performs an operation; and a universal cord 26 having one end connected to the operation section 24.

In the operation section 24, although described later, an erecting operation lever 27 that operates an erecting base 84 provided at a treatment tool lead-out portion 76 of the endoscopic observation portion 38, an air/water supply button 28a that opens and closes an air/water supply pipe line (not shown) from the water supply tank 21a, and a suction button 28b that opens and closes a suction pipe line (not shown) from the suction pump 21b are disposed side by side; and a pair of angle knobs 29, 29, and a treatment tool insertion port (forceps port) 30 are provided.

In this case, the water supply tank 21a is for storing washing water or the like that is supplied to the air/water supply pipe line in the ultrasonic endoscope 12 for washing the endoscopic observation portion 38 and so forth of the ultrasonic endoscope 12. Note that the air/water supply button 28a is used for ejecting gas such as the air and water such as the washing water that are supplied through the air/water supply pipe line from the water supply tank 21a, from the endoscopic observation portion 38 on the distal end side of the insertion section 22.

The suction pump 21b sucks the suction pipe line (not shown) for sucking the object to be sucked in the body cavity (including supplied washing water and so forth) from the distal end side of the ultrasonic endoscope 12. The suction button 28b is used for sucking the object to be sucked in the body cavity from the distal end side of the insertion section 22 with the sucking force by the suction pump 21b.

Also, the treatment tool insertion port 30 allows a treatment tool, such as forceps, a puncture needle, or a surgical knife, to be inserted therethrough.

The other end part of the universal cord 26 is provided with an ultrasonic connector 32a that is connected to the ultrasonic processor device 14, an endoscope connector 32b that is connected to the endoscopic processor device 16, and a light source connector 32c that is connected to the light source device 18. The ultrasonic endoscope 12 is removably connected to the ultrasonic processor device 14, the endoscopic processor device 16, and the light source device 18 respectively through the connectors 32a, 32b, and 32c. The light source connector 32c is also connected to an air/water supply tube 34a for connection with the water supply tank 21a, and a suction tube 34b for connection with the suction pump 21b.

The insertion section 22 is composed of, in order from the distal end side, the distal end part (distal end rigid part) 40 that is formed of a rigid member and has the ultrasonic observation portion 36 and the endoscopic observation portion 38; a bending part 42 that is connected to the proximal end side of the distal end part 40, that is formed of a plurality of bending pieces coupled to one another, and that is bendable; and a soft part 44 that couples the proximal end side of the bending part 42 with the distal end side of the operation section 24, and that is thin, long, and flexible.

As shown in FIG. 2, the bending part 42 has an angle ring structure in which a plurality of angle rings (nodal rings) 43 each formed in a ring-like shape are pivotally connected to one another in an axial direction. A plurality of operating wires (not shown) are disposed in the angle rings 43 at a predetermined interval in the axial direction of inner peripheral surfaces of the angle rings 43. The proximal ends of the operating wires are connected to a pulley (not shown) that is rotated by the pair of angle knobs 29, 29 provided at the operation section 24. Thus, when the pair of angle knobs 29, 29 are rotationally operated and the pulley is rotated, the operating wires are pulled and the bending part 42 bends in a desirable direction. By operating the pair of angle knobs 29, 29 as described above, the bending part 42 is remotely operated to bend and the distal end part 40 can be headed in a desirable direction.

In addition, a balloon into which an ultrasound conveyance medium (for example, water or oil) that covers the ultrasonic observation portion 36 is injected may be removably attached to the inside of the distal end part 40. Since ultrasonic waves and echo signals are markedly attenuated in the air, the balloon is inflated by injecting the ultrasound conveyance medium into the balloon, and the inflated balloon is brought into contact with an observation target region. Thus, the air is eliminated from the area between an ultrasonic vibrator (ultrasonic transducer) array 50 of the ultrasonic observation portion 36 and the observation target region, and the attenuation in ultrasonic waves and echo signals can be prevented.

The ultrasonic processor device 14 generates and supplies an ultrasonic signal (data) for causing the ultrasonic vibrator array 50 of the ultrasonic observation portion 36 of the distal end part 40 of the insertion section 22 of the ultrasonic endoscope 12 to generate ultrasonic waves. An echo signal (data) is reflected from the observation target region on which ultrasonic waves have been emitted. The ultrasonic processor device 14 receives and acquires the echo signal by using the ultrasonic vibrator array 50. The ultrasonic processor device 14 generates an ultrasound image that is displayed on the monitor 20 by performing various signal (data) processing on the acquired echo signal.

With the endoscopic processor device 16, the endoscopic observation portion 38 of the distal end part 40 of the insertion section 22 of the ultrasonic endoscope 12 receives and acquires a image signal (data) acquired from the observation target region illuminated with the illumination light from the light source device 18. The endoscopic processor device 16 generates an endoscope image that is displayed on the monitor 20 by performing various signal (data) processing and image processing on the acquired image signal.

The processor devices 14 and 16 may be composed of a processor of, for example, a personal computer (PC).

To image capture the observation target region in the body cavity by the endoscopic observation portion 38 of the ultrasonic endoscope 12 and to acquire an image signal, the light source device 18 generates illumination light, such as white light that consists of three primary colors of red light (R), green light (G), and blue light (B), or specific wavelength light; supplies the generated illumination light to the ultrasonic endoscope 12, the illumination light propagating on a light guide (not shown) or the like in the ultrasonic endoscope 12; emits the propagating light from the endoscopic observation portion 38 of the distal end part 40 of the insertion section 22 of the ultrasonic endoscope 12; and illuminates the observation target region in the body cavity.

The monitor 20 receives respective image signals generated by the ultrasonic processor device 14 and the endoscopic processor device 16, and displays an ultrasound image and an endoscope image. When the ultrasound image and the endoscope image are to be displayed, only one of the images may be selectively displayed, or both the images may be simultaneously displayed on the monitor 20. A monitor for displaying an ultrasound image and a monitor for displaying an endoscope image may be individually provided. Alternatively, an ultrasound image and an endoscope image may be displayed in any other desirable form.

The configurations of the distal end part and the bending part of the insertion section of the ultrasonic endoscope are described below in detail with reference to FIGS. 4 to 6, in addition to FIGS. 2 and 3.

Figure 4:
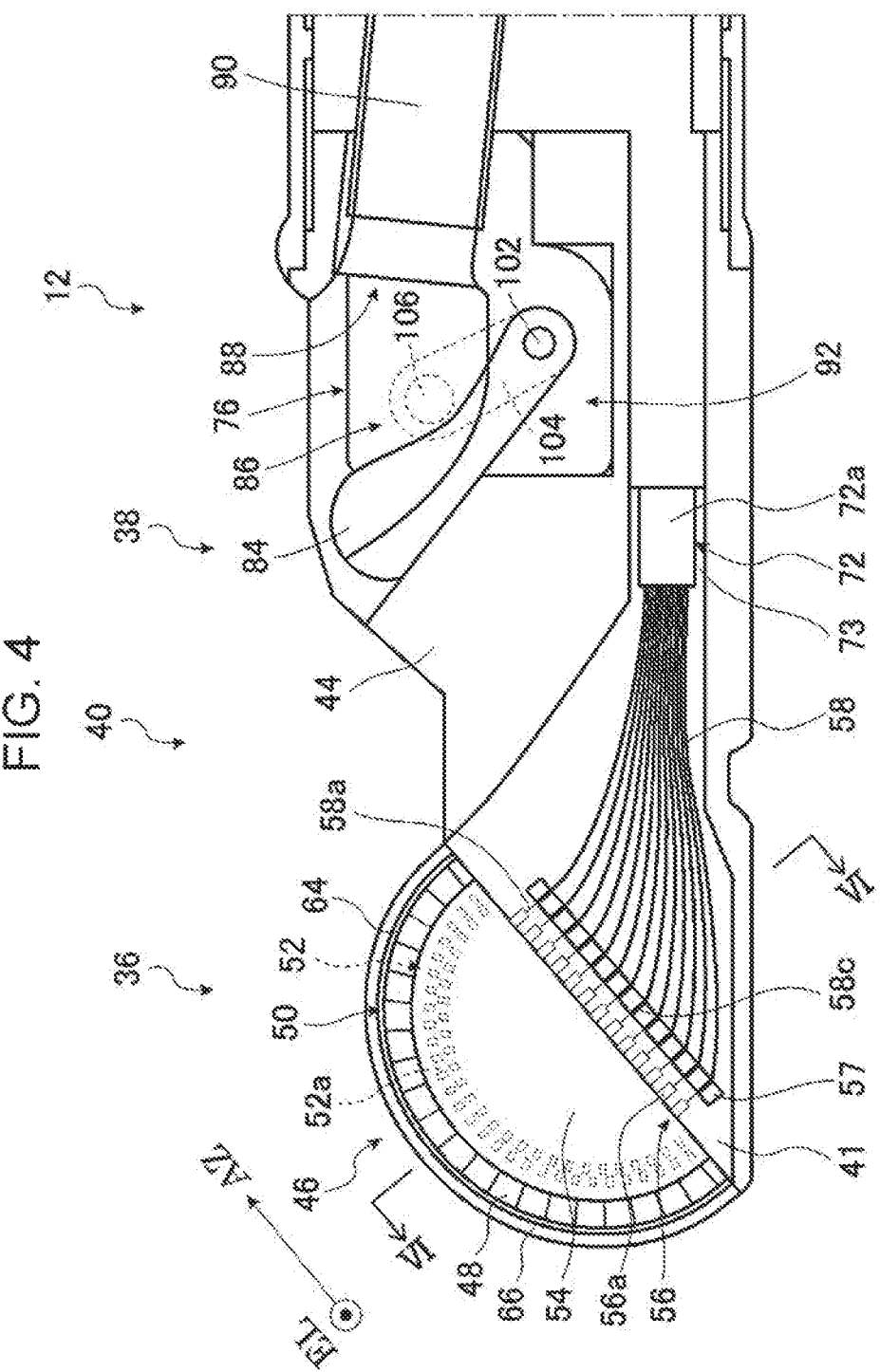
FIG. 4 is a schematic longitudinal section of the distal end part of the ultrasonic endoscope shown in FIG. 3 when cut along the center line in a longitudinal direction thereof.

FIG. 4 is a schematic longitudinal section of the distal end part of the ultrasonic endoscope shown in FIG. 3 when cut along the center line in a longitudinal direction thereof. FIG. 5 is a longitudinal section schematically showing an example of a heat release structure of the distal end part of the ultrasonic endoscope shown in FIG. 3 when cut in the longitudinal direction thereof. FIG. 6 is an arrow view taken along line VI-VI in FIG. 4, and is a transverse section schematically showing an example of the ultrasonic observation portion of the distal end part of the ultrasonic endoscope shown in FIG. 4.

As shown in FIGS. 2 to 3, the distal end part 40 of the ultrasonic endoscope 12 is provided with the ultrasonic observation portion 36 for acquiring an ultrasound image on the distal end side, and the endoscopic observation portion 38 for acquiring an endoscope image on the proximal end side. The ultrasonic observation portion 36 and the endoscopic observation portion 38 are attached to and held by an exterior member 41 made of a rigid member such as a hard resin and serving as a distal end main body of the distal end part 40 of the ultrasonic endoscope 12.

The ultrasonic observation portion 36 is composed of an ultrasonic vibrator unit 46, and the exterior member 41 to which the ultrasonic vibrator unit 46 is attached and by which the ultrasonic vibrator unit 46 is held.

The endoscopic observation portion 38 is composed of, for example, a treatment tool lead-out portion 76, an observation window 78, an illumination window 80 (80a, 80b), and a washing (air/water supply) nozzle 82. The treatment tool lead-out portion 76 is provided at the center of the endoscopic observation portion 38, and has the erecting base 84 that changes a protruding direction of a treatment tool, and an erecting base housing portion 86 that houses the erecting base 84 and has a recessed shape. Also, the erecting base housing portion 86 is provided with a treatment tool lead-out port 88 that leads the treatment tool to the outside. In the illustrated example, the endoscopic observation portion 38 has inclined surfaces 77a and 77b on both left and right sides of the treatment tool lead-out portion 76 when viewed from the ultrasonic observation portion 36 side on the distal end side. The inclined surfaces 77a and 77b face obliquely upper sides with respect to the distal end side. On the inclined surface 77a on the right side in the figure, the observation window 78, the washing nozzle 82, and the illumination window 80a are disposed sequentially from above. On the inclined surface 77b on the right side in the figure, the illumination window 80b is disposed.

In the example shown in FIG. 2, the treatment tool lead-out port 88 (or the treatment tool lead-out portion 76) is provided at the endoscopic observation portion 38. However, the present invention is not particularly limited to the illustrated example. The treatment tool lead-out port 88 may be provided at any location as far as the location is on the distal end side (the bending part 42 side) of the ultrasonic endoscope 12 with respect to the plurality of ultrasonic vibrators (48: see FIGS. 4 and 5) of the ultrasonic observation portion 36. For example, the treatment tool lead-out port 88 may be provided between the ultrasonic observation portion 36 and the endoscopic observation portion 38, or may be provided at a position further on the proximal end side with respect to the endoscopic observation portion 38.

That is, the ultrasonic endoscope to which the heat release structure according to the present invention is applied has to be an ultrasonic endoscope having a treatment tool lead-out port disposed on the proximal end side with respect to the ultrasonic vibrators.

The ultrasonic observation portion 36 is described next with reference to FIGS. 4 and 5.

Figure 5:
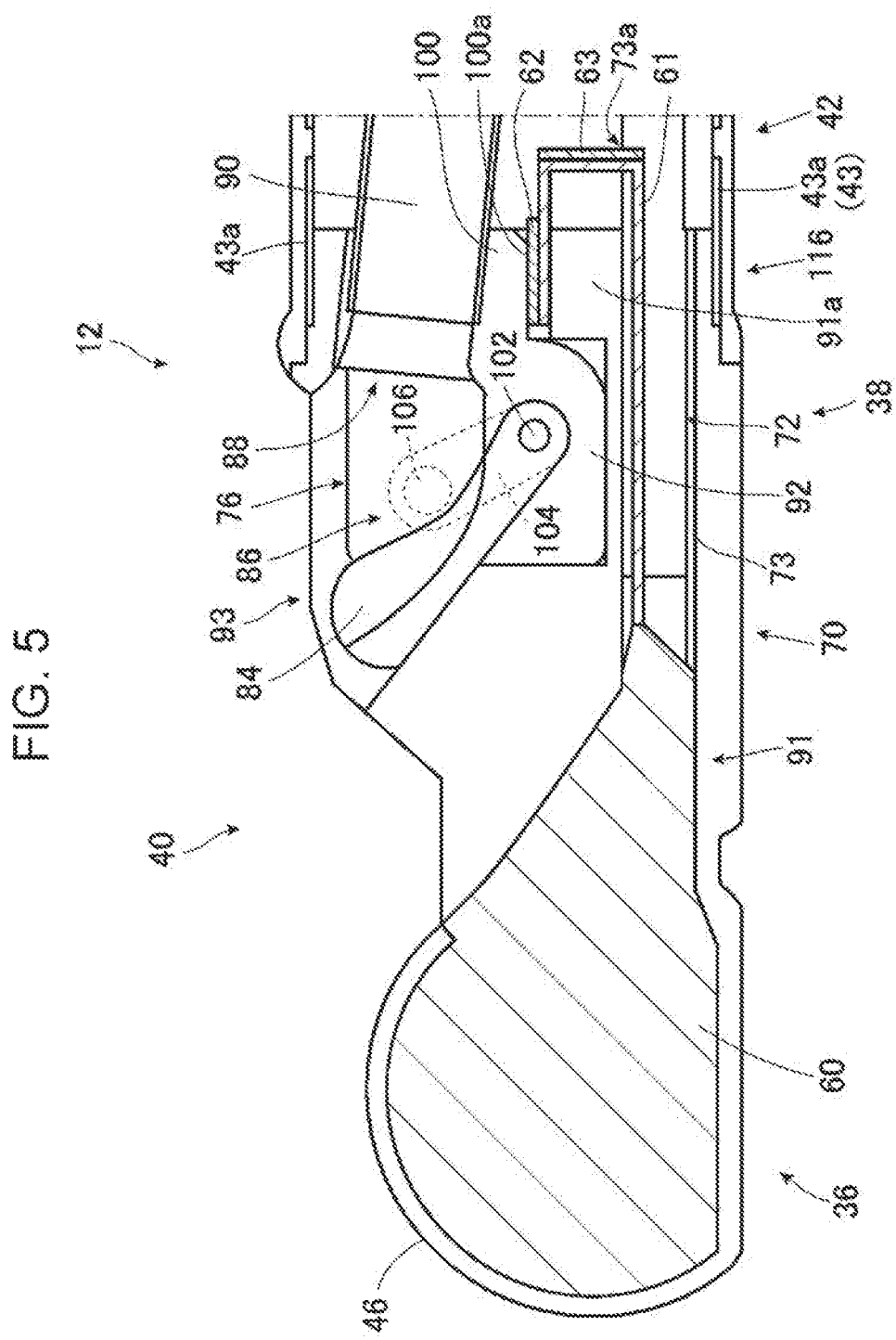
FIG. 5 is a longitudinal section schematically showing an example of a heat release structure of the distal end part of the ultrasonic endoscope shown in FIG. 3 when cut in the longitudinal direction thereof.

As shown in FIGS. 4 and 5, the ultrasonic vibrator unit 46 that constitutes the ultrasonic observation portion 36 has the ultrasonic vibrator array 50 consisting of the plurality of ultrasonic vibrators (transducers) 48, an electrode part 52 including a plurality of individual electrodes 52a, a cable wiring portion 56 including a plurality of connection portions 56a, a ground bar 57, and a copper foil 60.

As shown in FIG. 4, the electrode part 52 is provided on an outer surface or an inner surface of the ultrasonic vibrator array 50. The plurality of individual electrodes 52a of the electrode part 52 are individually connected to the plurality of ultrasonic vibrators 48. A backing material layer 54 supports the respective ultrasonic vibrators 48 of the ultrasonic vibrator array 50 from the lower surface side. The cable wiring portion 56 is electrically connected to the plurality of individual electrodes 52a of the electrode part 52. The plurality of connection portions 56a of the cable wiring portion 56 are connected to signal lines 58a of a plurality of coaxial cables 58 through wiring. The ground bar 57 is disposed below the backing material layer 54 on the side opposite to the ultrasonic vibrator array 50. The ground bar 57 is connected to shield members 58c of the plurality of coaxial cables 58.

As shown in FIG. 5, the copper foil 60 is a thermally conductive member connected to the ultrasonic vibrator array 50, is bonded to either surfaces, both outer side surfaces, or a rear surface side (on the side of the backing material layer 54 opposite to the ultrasonic vibrators 48) of the plurality of ultrasonic vibrators 48 or the backing material layer 54, and extends to the endoscopic observation portion 38 via the lower side of the backing material layer 54 on the side opposite to the ultrasonic vibrator array 50. The copper foil 60 shields the plurality of ultrasonic vibrators 48 and also releases the heat generated from the plurality of ultrasonic vibrators 48 and the backing material layer 54.

According to the first embodiment of the present invention, one end of an electrically/thermally conductive member 61 is connected to the copper foil 60; and the other end of the electrically/thermally conductive member 61, in the endoscopic observation portion 38, passes through a cable insertion hole 73 through which a shield cable 72 that binds the plurality of coaxial cables 58 being an ultrasonic cable according to the present invention is inserted, extends to the proximal end side of the endoscopic observation portion 38, passes through an opening 73a in an upper wall surface of the cable insertion hole 73, is folded back, extends to an erecting base assembly 92 composed of the erecting base 84 constituting the endoscopic observation portion 38, and is thermally connected to the erecting base assembly 92 via an electrically insulating thermally conductive member 62. In this case, the copper foil 60, the electrically/thermally conductive member 61, and the electrically insulating thermally conductive member 62 constitute a heat release structure 70 that is a feature of the present invention that releases the heat generated from the plurality of ultrasonic vibrators 48 and the backing material layer 54 to an erecting base component according to the present invention that is an electrically conductive endoscopic structure according to the present invention, for example, to a base portion 96 of the erecting base assembly 92 made of metal. The details of the heat release structure 70 will be described later.

Thus, with the heat release structure 70 that is a feature of the present invention, the heat generated from the plurality of ultrasonic vibrators 48 and the backing material layer 54 is released to the erecting base assembly 92 via the copper foil 60, the electrically/thermally conductive member 61, and the electrically insulating thermally conductive member 62. The heat transmitted to the erecting base assembly 92 may be further released to an angle sub-assembly according to the present invention of the bending part 42 that is an electrically conductive endoscopic structure according to the present invention electrically and thermally connected to the erecting base assembly 92, for example, the plurality of angle rings 43, a lever operating wire 110 that is an electrically conductive endoscopic structure according to the present invention, and/or an electrically conductive member in a forceps tube 114; and the heat may be further released from the operation section 24 to the outside of the subject via the insertion section 22.

According to the present invention, electrically connecting two members represents bringing the two members into direct contact with each other and fixing the two members to each other, or fixing the two members to each other by soldering or by joining the two members with an electrically conductive adhesive or the like, so as to allow electric current to smoothly flow between the two members.

Also, thermally connecting two members represents bringing the two members into direct contact with each other and fixing the two members to each other, or fixing the two members to each other by soldering or by joining the two members with an electrically conductive adhesive or the like, so as to transmit heat between the two members and to allow the heat to be smoothly transmitted from one member to the other member.

The ultrasonic vibrator unit 46 further has an acoustic matching layer 64 laminated on the ultrasonic vibrator array 50, and an acoustic lens 66 laminated on the acoustic matching later 64. That is, the ultrasonic vibrator unit 46 consists of a laminated body 68 of the acoustic lens 66, the acoustic matching later 64, the ultrasonic vibrator array 50, and the backing material layer 54.

The acoustic matching layer 64 is provided for acoustic impedance matching between a subject such as a human body and the ultrasonic vibrators 48.

The acoustic lens 66 attached on the acoustic matching layer 64 is for converging the ultrasonic waves emitted from the ultrasonic vibrator array 50 toward the object target portion. The acoustic lens 66 consists of, for example, a silicone-based resin (millable-based silicone rubber (HTV rubber), liquid silicone rubber (RTV rubber), or the like), a butadiene-based resin, a polyurethane-based resin, or the like. To secure the acoustic impedance matching between the subject and the ultrasonic vibrators 48 by the acoustic matching layer 64, and hence to increase transmittance of ultrasonic waves, the acoustic lens 66 has mixed therein powder of, for example, titanium oxide, alumina, or silica if required.

The ultrasonic vibrator array 50 is an array of a plurality of channels, for example, 48 to 192 channels (CH) consisting of a plurality of, for example, 48 to 192 rectangular-parallelepiped ultrasonic vibrators (transducers) 48 which are arranged in an arcuate form to face the outside.

That is, the ultrasonic vibrator array 50 consists of the plurality of ultrasonic vibrators 48 arranged in, for example, a one-dimensional array at a predetermined pitch, like the illustrated example. The ultrasonic vibrators 48 that constitute the ultrasonic vibrator array 50 are arranged at an equivalent interval in a protruding curve form in the axial direction of the distal end part 40 (longitudinal axial direction of the insertion section 22) as described above. Further, the ultrasonic vibrators 48 are successively driven on the basis of the driving signal input from the ultrasonic processor device 14. Thus, convex electronic scanning is performed in a range in which the ultrasonic vibrators 48 shown in FIG. 2 are arranged, as a scanning range.

The ultrasonic vibrator array 50 is disposed in an inclined manner such that the length thereof in the longitudinal direction of the ultrasonic vibrators 48 orthogonal to the AZ direction (EL (elevation) direction) is smaller than the length thereof in the parallel direction parallel to the bottom surface of the backing material layer 54 (AZ (azimuth) direction) and that the rear end side thereof protrudes. As shown in FIG. 6, the ultrasonic vibrators 48 have a configuration in which electrodes are formed on a bottom surface of a piezoelectric thick film of, for example, lead zirconate titanate (PZT) or polyvinylidene fluoride (PVDF). One of the electrodes is the individual electrode 52a individually and independently provided for each of the ultrasonic vibrators 48, and the other electrode is the common electrode (for example, ground electrode) 52b common to all the ultrasonic vibrators 48. In the illustrated example, the plurality of individual electrodes 52a are individually provided at lower surfaces on the inner sides of the plurality of ultrasonic vibrators 48, and are individually electrically connected to a plurality of wiring (not shown) of the cable wiring portion 56. Note that the plurality of wiring (not shown) of the cable wiring portion 56 are individually electrically connected to the plurality of connection portions 56a. In contrast, in the illustrated example, the common electrode 52b is provided on upper surfaces of end portions of the ultrasonic vibrators 48 and is connected to the ground bar 57. The plurality of individual electrodes 52a and the common electrode 52b constitute the electrode part 52.

Although not shown, the gap between two adjacent ultrasonic vibrators 48 is filled with a filling material such as an epoxy resin.

With the ultrasonic vibrator unit 46 of the ultrasonic observation portion 36, the respective ultrasonic vibrators 48 of the ultrasonic vibrator array 50 are driven, and a voltage is applied to both the electrodes 52a and 52b of the ultrasonic vibrators 48. When the voltage is applied, the piezoelectric bodies vibrate and successively generate ultrasonic waves, and emit the ultrasonic waves toward the observation target region of the subject. The plurality of ultrasonic vibrators 48 are successively driven using an electronic switch such as a multiplexer, and hence scanning is performed with the ultrasonic waves in a scanning range along a curved surface on which the ultrasonic vibrator array 50 is disposed, or for example, in a range by several tens of millimeters from the center of curvature radius of the curved surface. Consequently, each of the ultrasonic vibrators 48 of the ultrasonic vibrator array 50 generates heat when generates ultrasonic waves, and further the backing material layer 54 generates heat due to an effect of the ultrasonic waves.

Also, when the ultrasonic vibrator array 50 receives the echo signal (ultrasonic echo) reflected from the observation target region, the piezoelectric body vibrates and generates a voltage. The ultrasonic vibrator array 50 outputs the voltage, as an electric signal (ultrasound detection signal) corresponding to the received ultrasonic echo, to the ultrasonic processor device 14. The electric signal is subjected to various signal processing by the ultrasonic processor device 14, and then displayed as an ultrasound image on the monitor 20.

Figure 6:
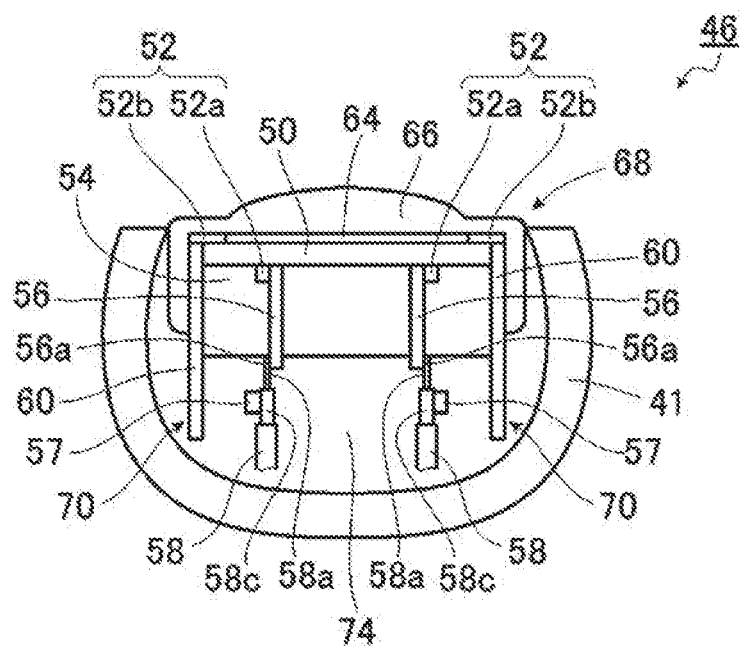
FIG. 6 is a transverse section schematically showing an example of an ultrasonic observation portion of the distal end part of the ultrasonic endoscope shown in FIG. 4.

As shown in FIGS. 4 and 6, the electrode part 52 consists of the plurality of (48 to 192) individual electrodes 52a that are provided in an arcuate form at a lower surface on the inner side of the ultrasonic vibrator array 50 (the respective ultrasonic vibrators 48) being perpendicular to the arcuate surface formed by the arrangement of the plurality of (48 to 192) ultrasonic vibrators 48, and that have electric continuity individually with the plurality of (48 to 192) ultrasonic vibrators 48. Note that the electrode part 52 may include the common electrode 52b of the plurality of ultrasonic vibrators 48. According to the present invention, being perpendicular is not limited to 90 degrees, and includes being substantially perpendicular, for example, 90±5 degrees, that is, angles in a range from 85 degrees to 95 degrees.

In FIG. 4, the plurality of individual electrodes 52a arranged in the arcuate form and the electrode part 52 consisting of the individual electrodes 52a are indicated by broken lines for easier understanding although these are hidden by the backing material layer 54 and are not actually viewed.

In the example shown in FIG. 6, the electrode part 52 is provided in two rows at the lower surface on the inner side of the ultrasonic vibrator array 50 being perpendicular to the arrangement surface of the plurality of ultrasonic vibrators 48. However, when the number of the ultrasonic vibrators 48 is small, the number of rows may be one, of when the plurality of ultrasonic vibrators 48 are arranged in multiple rows in the longitudinal direction, the number of rows may be two ore more. The electrode part 52 may be also provided at both outer side surfaces or either outer side surface in the longitudinal direction of the ultrasonic vibrator array 50, in addition to the lower surface on the inner side of the ultrasonic vibrator array 50. Alternatively, the electrode part 52 may be provided at the lower surface on the inner side of the ultrasonic vibrator array 50 by one row or more, and at either or both outer side surfaces of the ultrasonic vibrator array 50.

A larger number of the ultrasonic vibrators 48 is more preferable, and hence the plurality of individual electrodes 52a are preferably provided in multiple rows at the lower surface on the inner side of the ultrasonic vibrator array 50, and/or at both outer side surfaces of the ultrasonic vibrator array 50.

In the example shown in FIG. 6, the plurality of individual electrodes 52a are composed of individual electrodes provided on the end surface side in the longitudinal direction of the respective ultrasonic vibrators 48; however, the present invention is not limited thereto. Electrodes that are different from the individual electrodes 52a and that are connected to the individual electrodes 52a through wiring may be employed as long as the electrodes have electric continuity with the individual electrodes 52a of the ultrasonic vibrators 48. Also, while the electrode part 52 directly includes the common electrode, the electrode part 52 may include an electrode connected to the common electrode 52b through wiring.

The plurality of individual electrodes 52a and the common electrode 52b of the electrode part 52 are preferably provided as electrode pads.

As shown in FIGS. 4 and 6, the backing material layer 54 consists of a backing material disposed on the inner side with respect to the arrangement surface of the plurality of ultrasonic vibrators 48, that is, at the rear surface (lower surface) of the ultrasonic vibrator array 50, and is a layer of a member that supports the plurality of ultrasonic vibrators 48 arranged in the array form. The backing material layer 54 has an upper surface (upper side surface) formed in a shape with a protruding arcuate section.

In the example shown in FIG. 6, the backing material layer 54 has a configuration in which a plurality of wiring (not shown) of the cable wiring portion 56 connected to the plurality of individual electrodes 52a of the electrode part 52 are embedded therein. The plurality of connection portions 56a of the cable wiring portion 56 protrude downward from the backing material layer 54.

The backing material that constitutes the backing material layer 54 functions as a cushion material that flexibly supports the respective ultrasonic vibrators 48 of the ultrasonic vibrator array 50. Hence, the backing material consists of a material having stiffness such as hard rubber, and an ultrasound attenuating material (ferrite, ceramic, etc.) is added to the material if required.

Thus, the ultrasonic vibrator array 50 is configured such that, in the illustrated example, the plurality of rectangular-parallelepiped ultrasonic vibrators 48 are arranged on the arcuate outer surface which is the upper surface with the protruding arcuate section of the cylindrical backing material layer 54, in such a way that the longitudinal directions of the ultrasonic vibrators 48 extend parallel to each other, preferably at an equivalent interval. In other words, the ultrasonic vibrator array 50 is configured such that the plurality of ultrasonic vibrators 48 are arranged in an arcuate form to face outward.

The cable wiring portion 56 has the plurality of wiring (not shown) electrically connected to the plurality of individual electrodes 52a of the electrode part 52, and the plurality of connection portions 56a that are individually connected to the plurality of wiring (not shown) and that connect the wiring of the signal lines 58a of the plurality of coaxial cables 58.

The cable wiring portion 56 may include the plurality of connection portions 56a at end portions of the plurality of wiring (not shown) electrically connected to the plurality of individual electrodes 52a of the electrode part 52.

However, for easy connection to the plurality of individual electrodes 52a of the electrode part 52, the cable wiring portion 56 is preferably composed of a circuit board, for example, a flexible printed circuit (hereinafter, merely referred to as FPC), a printed circuit board (hereinafter, PCB), or a printed wired board (hereinafter, PWB). As shown in FIGS. 3 and 4, the cable wiring portion 56 preferably has a plurality of (48 to 192) wiring for electric connection individually with the plurality of (48 to 192) individual electrodes 52a of the electrode part 52, and a plurality of connection portions 56a that are individually connected to the plurality of (48 to 192) wiring.

In this case, the cable wiring portion 56 may be composed of a single circuit board, for example, a flexible circuit board such as FPC; or a rigid circuit board, such as PCB or PWB. Further, the cable wiring portion 56 may be composed of a multilayer circuit board in which a flexible circuit board such as FPC; and a rigid circuit board, such as PCB or PWB, are integrated. For example, as the cable wiring portion 56, one in which FPC having a plurality of (48 to 192) wiring for electrically connecting the plurality of (48 to 192) individual electrodes 52a of the electrode part 52, and a rigid circuit board having a plurality of (48 to 192) connection portions 56a for connecting the signal lines 58a of the plurality of coaxial cables 58 through wiring are integrated such that the plurality of (48 to 192) wiring are individually connected to the plurality of (48 to 192) connection portions 56a may be used.

Thus, the plurality of wiring of the cable wiring portion 56 can be easily individually electrically connected to the plurality of individual electrodes 52a of the electrode part 52 of the ultrasonic vibrator array 50.

In this case, the electric connection between the plurality of wiring of the cable wiring portion 56 and the plurality of individual electrodes (electrode pads) 52a of the electrode part 52 of the ultrasonic vibrator array 50 may be provided by using an anisotropic electrically conductive sheet or anisotropic electrically conductive paste, or may be provided by heat seal. The electric connection is not limited to the above-described connection method, and may use any method as far as the connection method does not degrade workability of wiring and does not raise the degree of difficulty of working processes. Specifically, a known method, such as wire bonding or soldering, may be used.

Accordingly, an ultrasonic endoscope using an ultrasonic vibrator unit having a wiring structure can be provided in which the wiring work for the ultrasonic vibrators can be improved in simplification, efficiency, and workability; the ultrasonic vibrator array can be downsized; workability is good when the respective electrodes of the ultrasonic vibrator array are connected to the multiple cables through wiring; the level of difficulty of the working process is low; a load is less applied to the cables; and the risk of disconnection is low.

Figure 7:
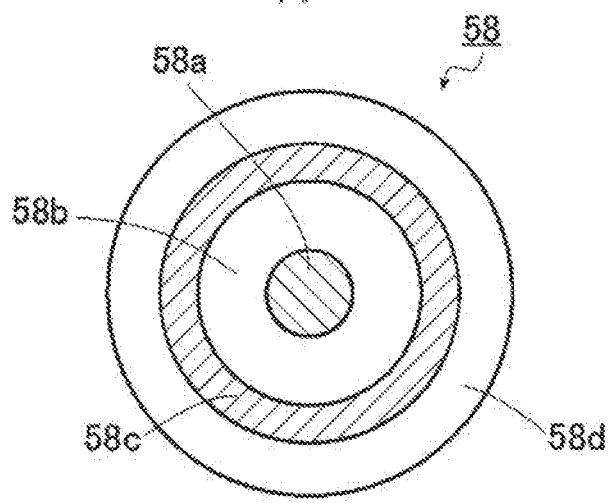
FIG. 7 is a cross section schematically showing a configuration of an example of a coaxial cable that is used for an ultrasonic observation portion of the distal end part of the ultrasonic endoscope shown in FIG. 4.

As shown in FIG. 7, the coaxial cable 58 used for the present invention includes a signal line 58a at the center, a first electrically insulating layer 58b on the outer periphery of the signal line 58a, a shield member 58c on the outer periphery of the first electrically insulating layer 58b, and a second electrically insulating layer 58d on the outer periphery of the shield member 58c. In other words, the coaxial cable 58 is configured such that the signal line 58a, the first electrically insulating layer 58b, the shield member 58c, and the second electrically insulating layer 58d are coaxially laminated from the center side.

Figure 8:
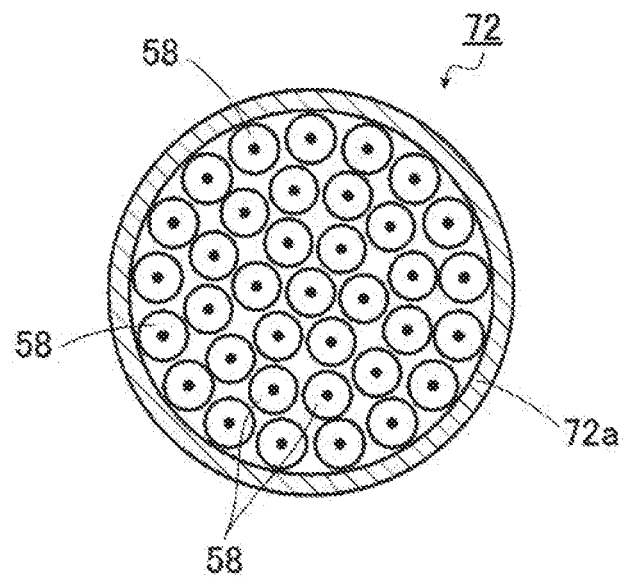
FIG. 8 is a cross section schematically showing an example of a shield cable composed of a plurality of coaxial cables that are used for the ultrasonic observation portion of the distal end part of the ultrasonic endoscope shown in FIG. 4.

In this case, according to the present invention, as shown in FIG. 8, the plurality of coaxial cables 58 are covered with an outer cover 72a at the outermost layer, and used as a single shield cable 72.

Note that the shield cable consisting of the plurality of ultrasonic cables used for the present invention is not limited to the shield cable 72 in which the plurality of coaxial cables 58 are covered with the outer cover 72a. For example, the shield cable may be a non-coaxial cable configured such that a plurality of signal lines each of which includes a central conductor and an electrically insulating layer of a dielectric or the like that covers the outer periphery of the central conductor, and a plurality of drain lines consisting of a conductor that functions as a shield member are disposed in a randomly mixed manner and serve as a single cable unit. Alternatively, the shield cable may be a non-coaxial cable configured such that a plurality of signal lines each of which includes a central conductor and an electrically insulating layer of a dielectric or the like that covers the outer periphery of the central conductor are disposed on the center side, a plurality of external conductors that function as a shield member are disposed around the plurality of signal lines, and the entirety is covered with a shielding material so as to serve as a single cable unit.

As shown in FIG. 4, the ground bar 57 provides electrical connection to the shield members 58c of the plurality of coaxial cables 58 of the single shield cable 72.

That is, the ground bar 57 functions as a ground portion that is connected to the common electrode 52b of the electrode part 52, for the signal lines 58a of the plurality of coaxial cables 58 that are individually electrically connected to the plurality of individual electrodes 52a of the electrode part 52. The ground bar 57 is electrically connected to the plurality of shield members 58c of the plurality of coaxial cables 58 and causes the potential of the ground portion to meet the potential of the plurality of shield members 58c.

The ground bar 57 may be any ground bar as long as the plurality of shield members 58c of the plurality of coaxial cables 58 can be electrically connected to the ground bar by, for example, soldering, and as long as the ground bar is a known ground bar used for an ultrasonic endoscope.

For electric connection to the ground bar 57 of the plurality of shield members 58c and for electric connection to the plurality of connection portions 56a of the cable wiring portion 56 of the plurality of signal lines 58a, the outer cover 72a on the distal end side of the single shield cable 72 is stripped off and removed, and the plurality of coaxial cables 58 are taken out. The second electrically insulating layers 58d on the distal end side of the plurality of taken-out coaxial cables 58 are stripped off and removed, and the plurality of shield members 58c are exposed to the outside. Distal end portions of the plurality of shield members 58c exposed to the outside are cut and removed while proximal end sides of the shield members 58c remain without being removed, and distal end portions of the first electrically insulating layers 58b are stripped off and removed. Hence the plurality of signal lines 58a are exposed to the outside.

Thus, the plurality of shield members 58c remaining while being exposed to the outside of the plurality of coaxial cables 58 are electrically connected to the ground bar 57 by soldering or other method.

Also, the plurality of signal lines 58a exposed to the outside at the distal ends of the plurality of coaxial cables 58 are individually electrically connected to the plurality of connection portions 56a of the cable wiring portion 56 by soldering or other method.

The copper foil 60 is disposed on the outer side surfaces of the plurality of ultrasonic vibrators 48 of the ultrasonic vibrator array 50, and takes roles of a shield effect and a heat release effect. The copper foil 60 constitutes the heat release structure 70 together with the electrically/thermally conductive member 61 and the electrically insulating thermally conductive member 62. The copper foil 60 is bonded to the plurality of ultrasonic vibrators 48 of the ultrasonic vibrator array 50, and is disposed on at least a side surface of the ultrasonic vibrator array 50, that is, an outer side surface of the laminated body 68, or more specifically outer side surfaces of the ultrasonic vibrator array 50 and the backing material layer 54.

Connection of the copper foil 60 to the plurality of ultrasonic vibrators 48 may be performed by bonding the copper foil 60 to outer side surfaces of the ultrasonic vibrator array 50 and the backing material layer 54. The copper foil 60 is bonded preferably by using an electrically conductive member, such as solder, silver paste, or an electrically conductive adhesive, or a silicone-based electrically non-conductive adhesive.

With the ultrasonic vibrator unit 46 shown in FIG. 6, the heat release structure 70 having the copper foil 60 is provided on both outer side surfaces of the laminated body 68 (the plurality of ultrasonic vibrators 48 and the backing material layer 54); however, the present invention is not limited thereto. The heat release structure 70 may be provided only on either outer side surface of the laminated body 68.

In this case, as shown in FIG. 6, when the ultrasonic vibrator unit 46 is attached to the exterior member 41 of the distal end part 40 of the ultrasonic endoscope 12 according to the present invention, a gap (space) between the backing material layer 54 of the laminated body 68 of the ultrasonic vibrator unit 46 and the cable wiring portion 56, a gap (space) among the copper foil 60, the ground bar 57, and the plurality of coaxial cables 58 (the signal lines 58a, the shield members 58c, and so forth), and a gap (space) among the laminated body 68, the copper foil 60, the ground bar 57, the plurality of coaxial cables 58, the backing material layer 54, and the exterior member 41 are preferably filled with a filling material having high heat release effect, and the filling material preferably forms a filling material layer 74. The filling material that forms the filling material layer 74 may use any filling material as long as the filling material is an electrically non-conductive filling material, such as an epoxy resin or a silicone-based filling material.

Such a filling material layer 74 is provided to fill a gap between the ultrasonic vibrator unit 46 and the exterior member 41, and more particularly a gap between the backing material layer 54 and the exterior member 41. The filling material layer 74 fixes the cable wiring portion 56 to wiring portions and part of extension portions of the plurality of coaxial cables 58, and hence can prevent occurrence of faulty connection of the signal lines 58a of the coaxial cables 58 at the plurality of connection portions 56a of the cable wiring portion 56, occurrence of faulty connection of the shield members 58c of the coaxial cables 58 at the ground bar 57, and disconnection of the coaxial cables 58 and so forth. As described above, since the cable wiring portion 56 and at least part of the plurality of coaxial cables 58 are covered with the filling material with high heat release effect and the filling material layer 74 is formed, the ultrasonic vibrator unit 46 of the distal end part 40 of the ultrasonic endoscope 12 according to the present invention, and the portions of the plurality of coaxial cables 58 when the assembly of the ultrasonic observation portion 36 is handled can be protected.

Further, the acoustic impedance of the filling material layer 74 preferably matches the acoustic impedance of the backing material layer 54 so that ultrasonic waves which have been oscillated from the ultrasonic vibrator array 50 and propagated below are not reflected at the boundary with respect to the backing material layer 54, and the ultrasonic waves which have been oscillated from the ultrasonic vibrator array 50 are reflected at the observation target or the periphery thereof and the ultrasonic waves which have propagated below the ultrasonic vibrator array 50 can be sufficiently attenuated. Hence, when the acoustic impedance of the filling material layer 74 is Zp (kg/m$^2$ s) and the acoustic impedance of the backing material layer 54 is Zb (kg/m$^2$ s), an acoustic impedance reflectivity Q (%) between the filling material layer 74 and the backing material layer 54 expressed in Expression (1) is preferably 50% or lower.

$$Q=100\times|Zp-Zb|/(Zp+Zb) \tag{1}$$

The acoustic impedance reflectivity Q is an index that expresses easiness of reflection of ultrasonic waves (acoustic beams) at the interface between the filling material layer 74 and the backing material layer 54. That is, as the value is closer to 0%, this indicates that the acoustic impedance of the filling material layer 74 more closely matches the acoustic impedance of the backing material layer 54. If the acoustic impedance reflectivity is about 50% or lower, the noise caused by the ultrasonic waves which have propagated below the ultrasonic vibrator array 50 can be processed so as not to adversely affect generation of an ultrasound image by the ultrasonic processor device 14 by using the ultrasonic signal received by the ultrasonic vibrator array 50.

Also, when the ultrasonic vibrator array 50 of the ultrasonic vibrator unit 46 oscillates ultrasonic waves, the driving signal transmitted from the ultrasonic processor device 14 to the ultrasonic vibrator array 50 becomes thermal energy. The ultrasonic vibrator array 50 generates heat due to the thermal energy, and hence the filling material layer 74 preferably has heat release effect. Thus, the filling material layer 74 preferably has a thermal conductivity of 1.0 W/mK or higher.

The ultrasonic observation portion 36 of the distal end part 40 of the ultrasonic endoscope 12 according to the present invention is configured as described above.

As shown in FIGS. 2 to 5, the endoscopic observation portion 38 is composed of, for example, the treatment tool lead-out portion 76, the observation window 78, the illumination windows 80 (80a, 80b), and the washing nozzle 82.

The observation window 78 is attached to face upward of the inclined surface 77a on the right side in the figure of the distal end part 40. Although not shown, an objective lens and a solid-state imaging element are disposed inside the observation window 78. The reflected light of an observation target region incident through the observation window 78 forms, with the objective lens, an image on an imaging surface of the solid-state imaging element. The solid-state imaging element photoelectrically converts the reflected light of the observation target region, the reflected light which has been transmitted through the observation window 78 and the objective lens and has formed an image on the imaging surface, into an image signal and outputs the image signal. The solid-state imaging element may be a charge coupled device (CCD), complementary metal oxide semiconductor (CMOS), or the like. The image signal output from the solid-state imaging element is transmitted to the endoscopic processor device 16 through the universal cord 26 via wiring cables (not shown) extending from the insertion section 22 to the operation section 24. The endoscopic processor device 16 performs various signal processing and image processing on the transmitted image signal, and displays the processed image signal as an endoscope optical image on the monitor 20.

The illumination windows 80 (80*a*, 80*b*) are provided on both sides with the treatment tool lead-out portion 76 interposed therebetween. The illumination windows 80 are connected to the emission end of a light guide (not shown). The light guide extends from the insertion section 22 to the operation section 24. The incident end of the light guide is connected to the light source device 18 connected through the universal cord 26. The illumination light emitted from the light source device 18 propagates through the light guide, and is emitted on an observation target region through the illumination windows 80.

Also, the washing nozzle 82 ejects the air or washing water from the water supply tank 21*a* via the air/water supply pipe line in the ultrasonic endoscope 12, to the observation window 78 and the illumination windows 80 (80*a*, 80*b*) for washing surfaces of the observation window 78 and the illumination windows 80.

Also, the treatment tool lead-out portion 76 having the erecting base 84 and the erecting base housing portion 86 is provided at the distal end part 40. The erecting base housing portion 86 is provided with the treatment tool lead-out port 88 that leads the treatment tool to the outside. The treatment tool lead-out port 88 is connected to a treatment tool channel 90 that is inserted through the inside of the insertion section 22. The treatment tool inserted into the treatment tool insertion port 30 is introduced from the treatment tool lead-out port 88 into a body cavity through the treatment tool channel 90. While the treatment tool lead-out port 88 is located at the endoscopic observation portion 38, if the motion of the treatment tool introduced into the body cavity from the treatment tool lead-out port 88 is checked using an ultrasound image, the treatment tool lead-out port 88 may be disposed at a position close to the ultrasonic observation portion 36.

The erecting base 84 is formed of a metal material such as stainless steel, and has a guide surface that is a recessed surface at the upper surface side. The guide surface is curved upward from the proximal end side toward the distal end side of the distal end part 40. The treatment tool led out from the treatment tool lead-out port 88 is curved upward with respect to the axial direction of the distal end part 40 (in the longitudinal axial direction of the distal end part 40) along the guide surface, and is led out from the upper side opening of the erecting base housing portion 86 to the outside.

Also, the erecting base 84 performs an erecting motion by an operation with the erecting operation lever 27 of the operation section 24. By causing the erecting base 84 to perform the erecting motion and hence adjusting the erecting angle from the tilted state, the lead-out direction (lead-out angle) of the treatment tool that is led out from the treatment tool lead-out portion 76 can be adjusted.

Note that the treatment tool lead-out port 88 also communicates with the suction channel. By operating the suction button 28*b* of the operation section 24, body fluid and so forth can be sucked from the treatment tool lead-out portion 76.

In this case, although the detailed drawing and description are omitted, the distal end part 40 can be disassembled into three separate blocks that are removably attached at the endoscopic observation portion 38. A first separate block is a proximal assembly 91 including the ultrasonic vibrator unit 46 that constitutes the ultrasonic observation portion 36, and the illumination windows 80 (80*a*, 80*b*) that constitute the endoscopic observation portion 38. A second separate block is the erecting base assembly 92 including the erecting base 84 that constitutes the treatment tool lead-out portion 76, and assembled on a center portion of the proximal assembly 91. A third separate block is a head assembly 93 including the observation window 78 that constitutes the endoscopic observation portion 38 and the washing nozzle 82, and assembled on the proximal assembly 91 while having therein the erecting base assembly 92.

The components of the proximal assembly 91 and the head assembly 93 are assembled to and held by a predetermined housing portion of the exterior member 41 that is formed of an electrically insulating resin material, for example, a plastic resin material, such as a methacrylate resin or a polycarbonate, and are fixed to the distal end part 40 together with the erecting base assembly 92.

The erecting base assembly 92 is described below with reference to FIGS. 9 and 10.

The erecting base assembly 92 includes the erecting base 84, and supports and drives the erecting base 84. Various sub-assemblies (described later) of the erecting base assembly 92 other than a gasket and a seal member are formed of a metal material such as stainless steel. The entirety of the erecting base assembly 92 has electrical conductivity (electroconductivity) and thermal conductivity, has electric continuity, receives transmitted heat, and transmits heat.

The erecting base assembly 92 is composed of the erecting base 84, and a driving mechanism portion 94 that drives the erecting base 84.

The driving mechanism portion 94 is composed of the base portion 96 that defines a recessed erecting base housing portion 86 and that rotatably supports the erecting base 84 from below, a lever housing portion 98 that is disposed at a side portion of the base portion 96 on the side-surface side of the erecting base housing portion 86, and a treatment tool insertion portion 100 that extends from the rear end side of the base portion 96 and the lever housing portion 98 and that includes the treatment tool lead-out port 88.

The entirety of the base portion 96, an outer wall portion of the lever housing portion 98, and the entirety of the treatment tool insertion portion 100 are integrally formed of a metal member.

A rotating shaft 102 is attached to a support portion 84*a* that protrudes downward from the erecting base 84. The rotating shaft 102 is rotatably supported at a shaft hole (not shown) of the base portion 96.

Thus, the erecting base 84 is coupled to the rotating shaft 102, and the erecting base 84 is rotatably supported by the base portion 96 via the rotating shaft 102 in the direction orthogonal to the axial direction of the distal end part 40. The erecting base 84 is configured to rotate (perform erecting motion) around the rotating shaft 102 in association with the rotation of the rotating shaft 102.

An erecting lever 104 that is a lever member is housed in a housing space 98a of the lever housing portion 98 of the driving mechanism portion 94.

The erecting lever 104 is formed in a long plate shape. One end portion side (proximal end portion side) in the longitudinal direction of the erecting lever 104 is coupled to the rotating shaft 102 of the base portion 96. Note that the rotating shaft 102 and the erecting lever 104 may be integrally formed, or may be separately formed and integrally coupled to each other.

The other end portion (distal end portion) of the erecting lever 104 has a columnar through hole 104a. A columnar member 106 having a diameter substantially the same as that of the through hole 104a is rotatably fitted into the through hole 104a. A lever operating wire 110 of a control cable 108 is attached the columnar member 106.

The control cable 108 is disposed so as to be inserted through the insertion section 22 from the operation section 24 of the ultrasonic endoscope 12. The distal end side of the control cable 108 is connected to a side wall portion 98b of the lever housing portion 98.

The control cable 108 is configured such that the lever operating wire 110 is slidably inserted into a tube of a flexible sleeve (guide tube) having a flexible tubular shape.

The lever operating wire 110 is formed of a stranded wire in which elemental wires formed of a plurality of metal thin wires are stranded. The flexible sleeve is formed by, for example, covering a tubular solid coil with a heat-shrinkable tube.

An end portion of the flexible sleeve is fixed to the side wall portion 98b of the lever housing portion 98, at a connection portion between the control cable 108 and the lever housing portion 98.

The lever operating wire 110 is inserted through a through hole (not shown) that is formed at the side wall portion 98b of the lever housing portion 98, is inserted into the housing space 98a of the lever housing portion 98, and is fixed to the columnar member 106.

Also, the proximal end side of the control cable 108 is connected via the erecting operation lever 27 and a power transmission mechanism in the operation section 24.

With this configuration, when the lever operating wire 110 advances and retracts (performs pushing and pulling motion) by a pushing and pulling operation with the erecting operation lever 27 of the operation section 24, the erecting lever 104 rotates (swings) around the rotating shaft 102, the erecting base 84 performs an erecting operation via the rotating shaft 102 in association with the rotation (swing), the erecting angle of the erecting base is changed, and hence the treatment tool is led out in a desirable direction. For example, as shown in FIG. 10, the erecting base 84 can perform the erecting motion in the range from the tilted state indicated by solid lines to the erecting state indicated by two-dot chain lines.

The treatment tool insertion portion 100 of the driving mechanism portion 94 has formed therein a treatment tool insertion hole 101 that extends therethrough in a columnar shape. The exit of the treatment tool insertion hole 101 serves as the treatment tool lead-out port 88. The distal end side of a cylindrical linking member 112 is inserted into and fixed to the treatment tool insertion hole 101. A distal end portion of a forceps tube 114 that forms the treatment tool channel 90 is fitted onto the rear end side of the linking member 112. The forceps tube 114 is connected to, for example, a forceps pipe that is made of SUS and that constitutes the treatment tool channel 90. The forceps tube 114 contains an electrically conductive member, such as a metal braiding, a mesh, or a solid coil spring.

Thus, the treatment tool that is inserted from the treatment tool insertion port 30 of the operation section 24 and inserted through the forceps tube 114 which serves as the treatment tool channel 90 is led out to the treatment tool lead-out port 88 via the linking member 112 and the treatment tool insertion hole 101.

The treatment tool led out to the treatment tool lead-out port 88 is erected by the erecting base 84 at a predetermined angle, and is led out to the outside from the treatment tool lead-out port 88.

The sub-assemblies of the erecting base assembly 92 configured as described above other than members, such as a gasket and a seal member, are formed of a metal material to obtain high intensity, and are entirely electrically and thermally conductive.

Figure 11:
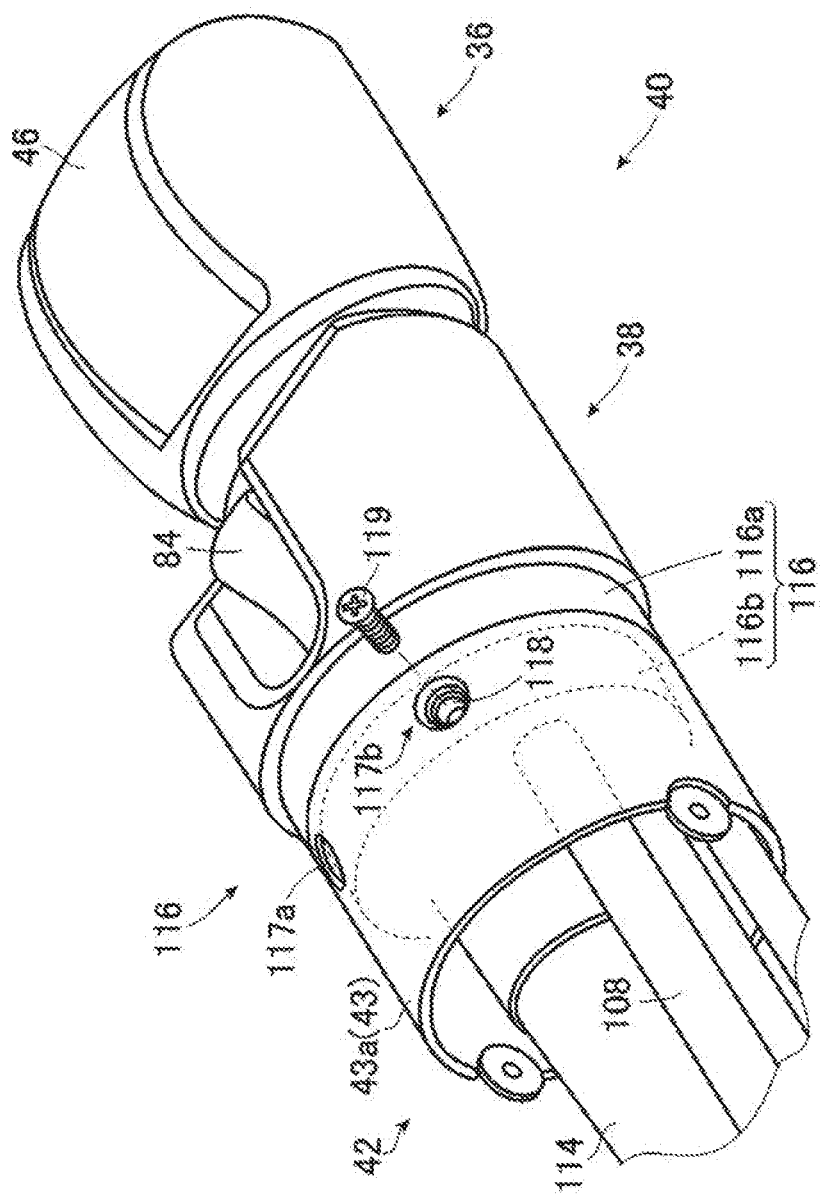
FIG. 11 is a partial exploded perspective view schematically showing a connecting portion between the erecting base assembly of the distal end part and the bending part shown in FIG. 2.

FIG. 11 is a perspective view showing a configuration of a connecting portion 116 between the endoscopic observation portion 38 of the distal end part 40 and the bending part 42.

In the ultrasonic endoscope 12 according to this embodiment, the connecting portion 116 with respect to the bending part 42 is formed at an outer peripheral portion on the proximal end side of the endoscopic observation portion 38 of the distal end part 40. The connecting portion 116 has an intermediate diameter portion 116a at which the outer peripheral surface of the distal end part 40 is smaller than the diameter on the distal end side, and a small diameter portion 116b with a smaller diameter than that of the intermediate diameter portion 116a, on the proximal end side of the intermediate diameter portion 116a.

The angle ring 43 (hereinafter, referred to as distal end ring 43a) at the distal end of the bending part 42 of the ultrasonic endoscope 12 is fitted onto an outer peripheral portion of the small diameter portion 116b of the connecting portion 116. The distal end ring 43a of the bending part 42 is a distal-end-side ring component of an angle sub-assembly according to the present invention. As shown in FIG. 2, the distal end ring 43a is the most distal angle ring among the plurality of annular angle rings 43 disposed in a rotatably coupled manner at the bending part 42.

The small diameter portion 116b of the connecting portion 116 has a plurality of screw holes (not shown) and at least one opening (not shown). The distal end ring 43a has a plurality of openings 117a corresponding to the plurality of screw holes of the small diameter portion 116b, and at least one opening 117b corresponding to the at least one opening of the small diameter portion 116b.

Screws (not shown) are screwed into the plurality of openings 117a of the distal end ring 43a, and are screwed into the plurality of screw holes of the small diameter portion 116b. Thus, the distal end ring 43a is fixed to the small diameter portion 116b of the connecting portion 116.

Figure 9:
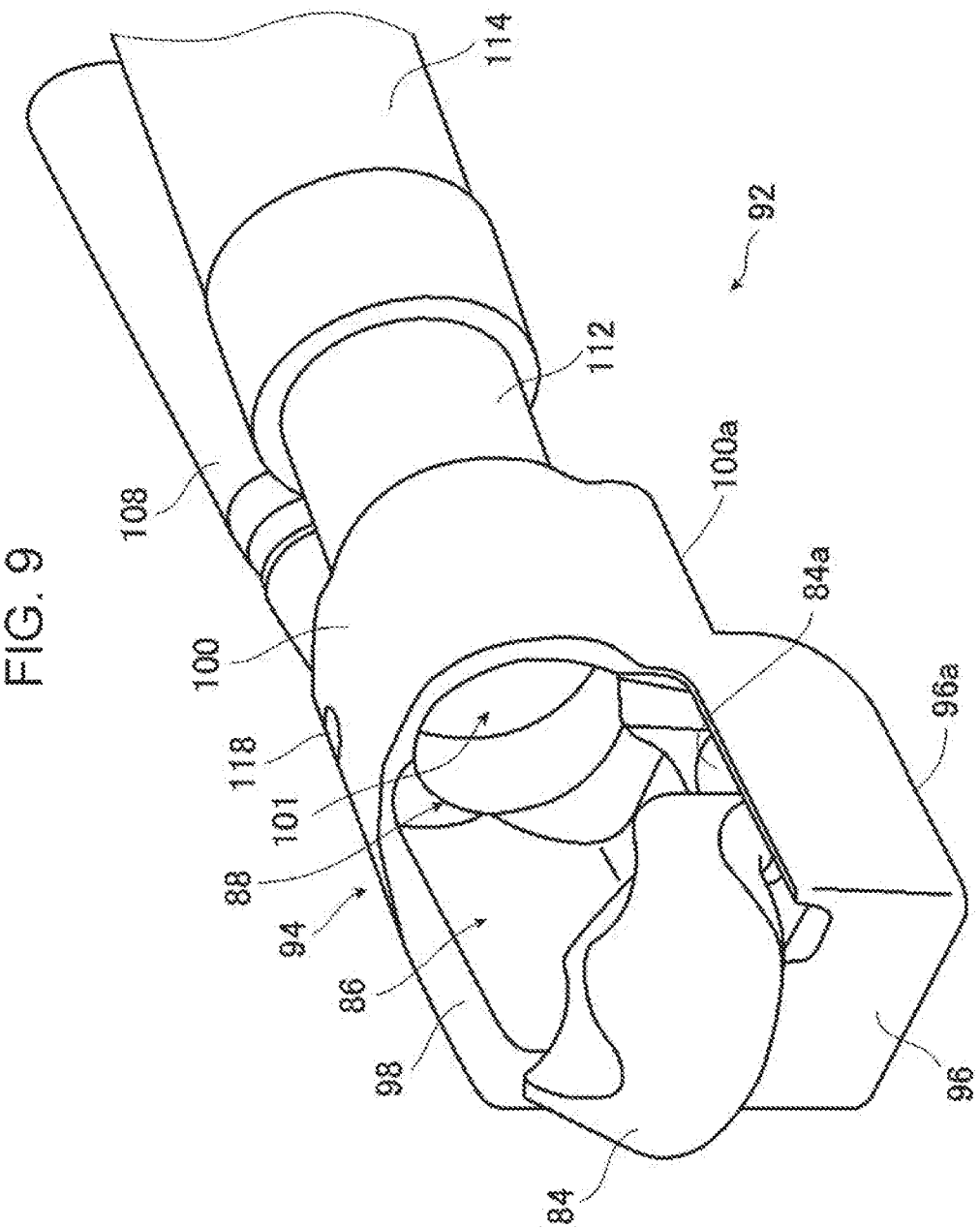
FIG. 9 is a perspective view schematically showing an example of an erecting base assembly of the distal end part shown in FIG. 2.
Figure 10:
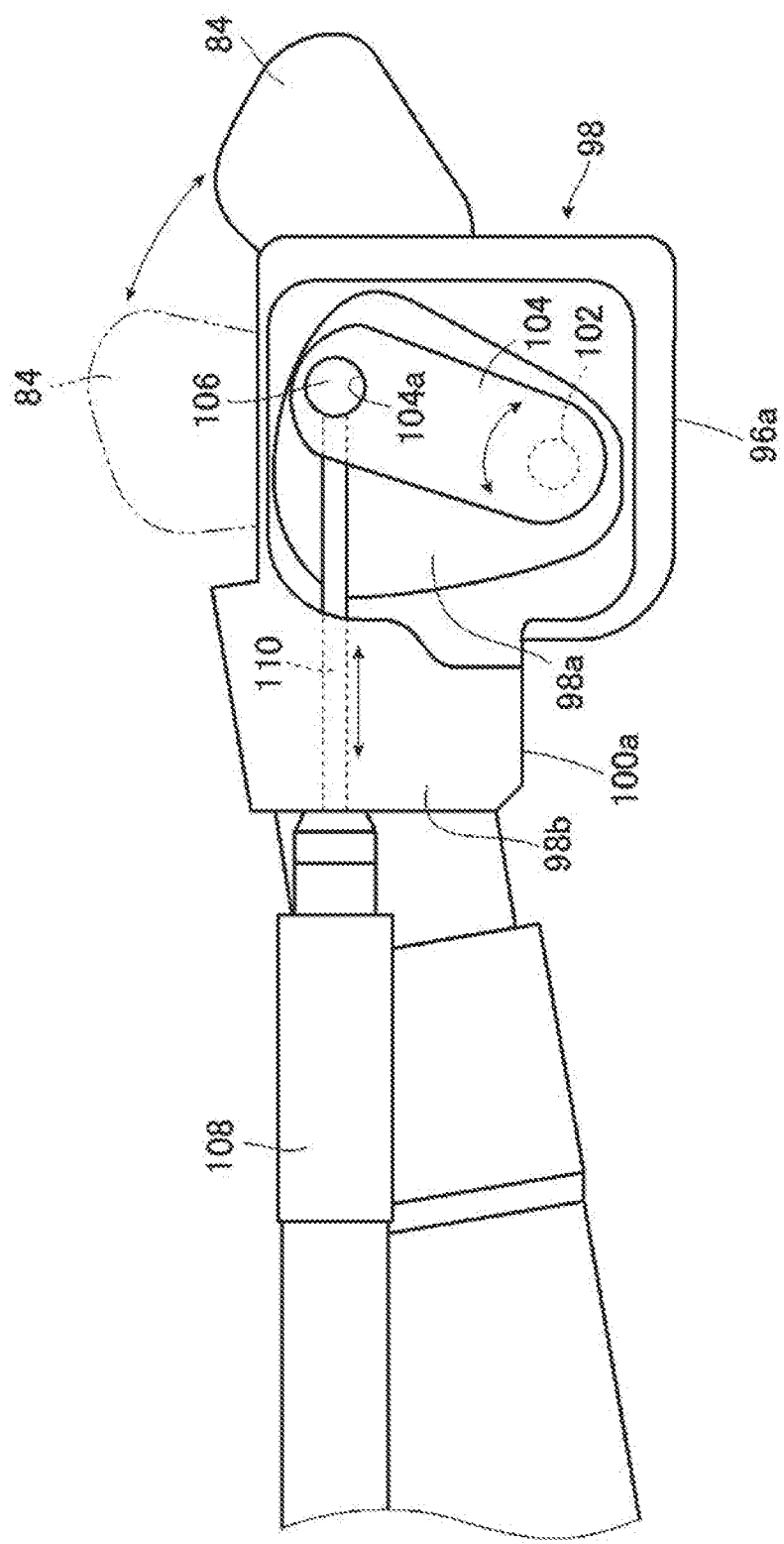
FIG. 10 is a side view showing an erecting lever of a lever housing portion of the erecting base assembly shown in FIG. 9.

In contrast, the outer surface (upper surface) of the treatment tool insertion portion 100 of the driving mechanism portion 94 of the erecting base assembly 92 has at least one screw hole 118 as shown in FIG. 9 corresponding to the at least one opening of the small diameter portion 116b of the connecting portion 116. An electrically conductive, for example, a metal screw 119 is screwed into the at least one opening of the small diameter portion 116b corresponding to the at least one opening 117b of the distal end ring 43a, and is fastened into the at least one screw hole 118 of the treatment tool insertion portion 100. Thus, the distal end ring 43a and the small diameter portion 116b of the connecting portion 116 are fixed to the treatment tool insertion portion 100 of the driving mechanism portion 94 of the erecting base assembly 92.

Accordingly, the erecting base assembly 92 made of metal of the treatment tool lead-out portion 76 is electrically and thermally connected to the distal end ring 43a and the plurality of angle rings 43 of the bending part 42 via the screw 119 of the connecting portion 116 between the distal end part 40 and the bending part 42. Consequently, the erecting base assembly 92 is electrically and thermally connected to the ground of the operation section 24 via a metal outer tube (not shown) from the angle rings 43 to the soft part 44.

When a high-frequency treatment tool is used as a treatment tool that is led out from the treatment tool lead-out portion 76, even if electric current leaks from the treatment tool to the erecting base 84, the leaking current flows from the erecting base 84 to the angle rings 43 of the bending part 42 via the erecting base assembly 92, and the screw 119 of the connecting portion 116 between the distal end part 40 and the bending part 42, and then is released from the angle rings 43 to the ground of the operation section 24 via the metal outer tube of the soft part 44. Thus, the leaking current leaking from the treatment tool to the erecting base 84 can be properly released to the ground.

Also, with the heat release structure 70 according to the present invention, when the heat generated from the plurality of ultrasonic vibrators 48 is released to the erecting base assembly 92 of the treatment tool lead-out portion 76 via the copper foil 60, the electrically/thermally conductive member 61, and the electrically insulating thermally conductive member 62, the heat is released from the erecting base assembly 92 to the ground of the operation section 24 via the screw 119, the angle rings 43 of the bending part 42, and the metal outer tube of the soft part 44, like the leaking current. Thus, the heat transmitted from the plurality of ultrasonic vibrators 48 to the erecting base assembly 92 can be properly released to the ground, and can be released to the outside.

The heat release structure 70 of the ultrasonic endoscope 12 according to the first embodiment of the present invention is described with reference to FIG. 5.

FIG. 5 is a drawing that emphasizes the members and so force related to the heat release structure 70 to explain the heat release structure 70. FIG. 5 emphasizes the part required for the explanation, whereas simplifies or omits the part not used for the explanation.

As shown in FIG. 5, the heat release structure 70 consists of the copper foil 60, the electrically/thermally conductive member 61, and the electrically insulating thermally conductive member 62 as described above. The heat release structure 70 preferably additionally includes an electrically insulating coating member 63.

In this case, the copper foil 60 is bonded to the entirety of either side surfaces or the entirety of both outer side surfaces of the plurality of ultrasonic vibrators 48 and the backing material layer 54 of the ultrasonic vibrator unit 46 of the ultrasonic observation portion 36 of the proximal assembly 91. The copper foil 60 extends to below the backing material layer 54 on the side opposite to the ultrasonic vibrator array 50, and covers the entirety of the side surfaces of the ultrasonic observation portion 36.

The electrically/thermally conductive member 61 thermally connects the copper foil 60 and the electrically insulating thermally conductive member 62 to each other. One end, that is, an end portion on the distal end side of the electrically/thermally conductive member 61 is connected to a portion of the copper foil 60 extending to a position below the backing material layer 54. The other end, that is, an end portion on the proximal end side of the electrically/thermally conductive member 61 extends from the end portion on the distal end side which is the connection portion with respect to the copper foil 60 through the cable insertion hole 73 of the endoscopic observation portion 38 to the proximal end side of the endoscopic observation portion 38; is folded back through the opening 73a of the upper wall surface of the cable insertion hole 73, and extends to a lower surface 100a of the treatment tool insertion portion 100 of the driving mechanism portion 94 of the erecting base assembly 92 of the endoscopic observation portion 38; and is mounted and disposed on a support component 91a of the endoscopic observation portion 38 of the proximal assembly 91 that supports the erecting base assembly 92 at the position below the lower surface 100a.

The electrically insulating thermally conductive member 62 is mounted and disposed on the other end portion of the electrically/thermally conductive member 61 mounted on the support component 91a at the position below the lower surface 100a of the erecting base assembly 92.

That is, the other end portion of the electrically/thermally conductive member 61 and the electrically insulating thermally conductive member 62 are disposed in an overlapped manner, and are sandwiched between and fixed by the support component 91a of the proximal assembly 91 and the lower surface 100a of the erecting base assembly 92.

In this way, the electrically/thermally conductive member 61 is thermally connected to the erecting base assembly 92 via the electrically insulating thermally conductive member 62, but is electrically insulated or isolated from the erecting base assembly 92 via the electrically insulating thermally conductive member 62.

In this case, while the electrically insulating thermally conductive member 62 may be fixed to the electrically/thermally conductive member 61 or the erecting base assembly 92, the electrically insulating thermally conductive member 62 is preferably removably attached to at least one of the electrically/thermally conductive member 61 or the erecting base assembly 92. The distal end part 40 of the ultrasonic endoscope 12 can be disassembled into the proximal assembly 91, the erecting base assembly 92, and the head assembly 93. Sub-assemblies of the assemblies can be disassembled and repaired, thereby improving ease of repair of the ultrasonic endoscope 12 including the heat release structure 70.

The electrically/thermally conductive member 61 extends from the cable insertion hole 73, passes through the opening 73a of the upper wall surface of the cable insertion hole 73, is folded back, and is mounted and disposed on the support component 91a of the proximal assembly 91. The folded back portion that protrudes from the opening 73a of the cable insertion hole 73, that is folded back, and that extends to a position covered with the electrically insulating thermally conductive member 62 is open by the opening 73a of the cable insertion hole 73. Thus, the folded portion is an exposed portion exposed to other various endoscopic structures of the endoscopic observation portion 38, such as the forceps pipe made of SUS and so forth that constitutes the treatment tool channel 90. Thus, as shown in FIG. 5, according to the present invention, the folded back portion of the electrically/thermally conductive member 61, that is, the exposed portion is preferably covered with the electrically insulating coating member 63, and is electrically insulated or isolated from the endoscopic structures.

In the illustrated example, while the electrically/thermally conductive member 61 and the electrically insulating thermally conductive member 62 are sandwiched between the support component 91a of the proximal assembly 91 and the lower surface 100a of the erecting base assembly 92, the present invention is not limited thereto. The electrically/thermally conductive member 61 and the electrically insulating thermally conductive member 62 may be disposed between a portion of a surface of the erecting base assembly 92 and a support component thereof, such as between a lower surface of the base portion 96 of the erecting base assembly 92 and a support component of the endoscopic observation portion 38 of the proximal assembly 91, as long as being disposed between a surface of the erecting base assembly 92 and a support component thereof.

Also, the electrically insulating thermally conductive member 62 may be disposed at a portion or the entirety of outer surfaces of various erecting base components of the erecting base assembly 92. In the ultrasonic endoscope 12, the cable insertion hole 73 which is disposed at the proximal assembly 91 and through which the shield cable 72 is inserted passes through the bottom surface (lower surface) side of the erecting base assembly 92. Thus, the electrically insulating thermally conductive member 62 is preferably disposed on a bottom surface, or a side surface, or both the surfaces of the erecting base component of the erecting base assembly 92.

With the heat release structure 70 according to the first embodiment of the present invention, the copper foil 60 and the electrically/thermally conductive member 61 are thermally conductive members according to the present invention connected to the plurality of ultrasonic vibrators 48, and are connected to the electrically insulating thermally conductive member 62 that is connected to the erecting base assembly 92 that is an endoscopic structure according to the present invention.

The copper foil 60 is an electrically/thermally conductive member, and functions as a thermally conductive member that is connected to the plurality of ultrasonic vibrators 48. Preferably, the copper foil 60 is a first thermally conductive member that is directly connected to the plurality of ultrasonic vibrators 48, that is, an electrically conductive first thermally conductive member.

The copper foil 60 is not limited to the foil form, and preferably has a shape, such as a mesh form or a sheet form, that can sufficiently transmit heat from the side surfaces in the width direction of the ultrasonic vibrator array 50 and the backing material layer 54.

While the copper foil 60 is used for the thermally conductive member according to the present invention, for example, the first thermally conductive member, the present invention is not limited thereto. Any member with good thermal conductivity may be employed. For example, in a case of a thin plate-shaped body, a metal foil, such as an aluminum foil, a gold foil, or a silver foil may be used; or a metal sheet such as a sheet metal, for example, a copper sheet may be used. Alternatively, in a case other than a thin plate-shaped body, a member used for the electrically/thermally conductive member 61, which is described later, for example, a net member of a metal braiding, a metal mesh, or a cable including a core wire thicker than the signal line 58a of the coaxial cable 58 may be used.

Also, in the illustrated example, while the copper foil 60 is directly connected to the plurality of ultrasonic vibrators 48; however, the present invention is not limited thereto. The copper foil 60 may be connected to a substrate that is fixed to the plurality of ultrasonic vibrators 48 and/or a heat release plate, as long as the copper foil 60 has thermal conductivity.

The electrically/thermally conductive member 61 functions as a thermally conductive member that is connected to the plurality of ultrasonic vibrators 48, together with the copper foil 60. Preferably, the electrically/thermally conductive member 61 is a second thermally conductive member according to the present invention, that is an electrically conductive second thermally conductive member, whose one end or an end portion on the distal end side is connected to the copper foil 60 and the other end or an end portion on the proximal end side is connected to the electrically insulating thermally conductive member 62.

The electrically/thermally conductive member 61 is not particularly limited as long as the electrically/thermally conductive member 61 can transmit the heat which has been generated from the plurality of ultrasonic vibrators 48 and the backing material layer 54 and has been transmitted to the copper foil 60, to the endoscopic structure such as the erecting base assembly 92 via the electrically insulating thermally conductive member 62. Any member can be used as long as it has thermal conductivity and can be flexibly housed in a narrow space of the distal end part 40 of the ultrasonic endoscope 12. Since the electrically/thermally conductive member 61 is required to have thermal conductivity and to be flexibly housed in a narrow space such as the cable insertion hole 73, for example, a thermally conductive cable such as a cable having a core wire, a thermally conductive wire material such as a metal wire, a thermally conductive net such as a metal net member, or a member formed by extending part of the copper foil 60 as a wire material may be used.

As described above, the electrically/thermally conductive member 61 may be an electrically/thermally conductive member different from the copper foil 60, or may be a member extending from the copper foil 60. When an extending member from the copper foil 60 is used for the electrically/thermally conductive member 61, the thermally conductive member according to the present invention functions as a single thermally conductive member.

When a different thermally conductive member mentioned above is used as the electrically/thermally conductive member 61, to increase thermal transmission efficiency, it is preferable to use a cable including a core wire thicker than the signal line 58a of each coaxial cable 58, or a metal wire thicker than the signal line 58a.

When flexibility is desired for the electrically/thermally conductive member 61 so as to be housed in a narrow space, it is preferable to use a metal-bladed net member.

The first thermally conductive member such as the copper foil 60 and the second thermally conductive member such as the electrically/thermally conductive member 61 may be connected to each other by any connection method as long as thermal conductivity can be maintained. For example, connection by soldering, or connection using a thermally conductive weak adhesive may be employed.

In this case, the thermally conductive member according to the present invention, for example, the first thermally conductive member such as the copper foil 60 and the second thermally conductive member such as the electrically/thermally conductive member 61 preferably have a thermal conductivity of 0.5 W/mK or higher. If the thermal conductivity of these thermally conductive members is lower than 0.5 W/mK, the heat generated from the plurality of ultrasonic vibrators 48 and the backing material layer 54 cannot be efficiently released to the erecting base assembly 92 which is the endoscopic structure according to the present invention. This may increase the surface temperature of the ultrasonic vibrator unit 46, and may cause a moderate-temperature burn or the like to occur at a body cavity surface.

The electrically insulating thermally conductive member 62 is disposed between the electrically/thermally conductive member 61 supported by the support component 91*a* of the proximal assembly 91 and the lower surface 100*a* of the erecting base assembly 92, thermally connects the electrically/thermally conductive member 61 and the erecting base assembly 92 to each other, and electrically insulating or isolating the electrically/thermally conductive member 61 from the erecting base assembly 92.

The electrically insulating thermally conductive member 62 may use any member as long as the member thermally connects the electrically/thermally conductive member 61 and the erecting base assembly 92 to each other, and electrically insulates or isolates the electrically/thermally conductive member 61 from the erecting base assembly 92. The electrically insulating thermally conductive member may use, for example, heat release silicone rubber or a heat release sheet. To have thermal conductivity, a ceramic member, a heat release pad, or electrically insulating coating, such as diamond-like carbon (DLC) coating or paraffin coating may be used.

The electrically insulating thermally conductive member 62 preferably has a withstand voltage of 1.5 kV or higher. If the withstand voltage of the electrically insulating thermally conductive member 62 is lower than 1.5 kV, the electrically insulating thermally conductive member 62 cannot electrically insulate or isolate the electrically/thermally conductive member 61 from the erecting base assembly 92 which is the endoscopic structure. If an electric discharge or an electric leakage occurs at the erecting base assembly 92 which is the endoscopic structure due to use of a high-frequency treatment tool or the like, an electric leakage may occur at the surface of the ultrasonic vibrator unit 46 via the electrically/thermally conductive member 61 and the copper foil 60, thereby possibly applying a burden such as an electric shock to a body cavity surface, or causing a short and hence generating a moderate-temperature burn.

In addition, since the ultrasonic vibrators 48 are driven with high voltage, the high voltage is to be prevented from leaking to the erecting base assembly 92.

Also, the electrically insulating thermally conductive member 62 preferably has a thermal conductivity of 0.5 W/mK or higher. The reason is similar to the case of the copper foil 60 and the electrically/thermally conductive member 61 because the electrically insulating thermally conductive member 62 is required to transmit the heat generated from the plurality of ultrasonic vibrators 48 and the backing material layer 54 to the erecting base assembly 92 which is the endoscopic structure according to the present invention, like the electrically/thermally conductive member 61.

Also, the electrically insulating thermally conductive member 62 preferably has a thickness of 3 mm or smaller. The thickness of the electrically insulating thermally conductive member 62 is not particularly limited as long as the electrically insulating thermally conductive member 62 has thermal conductivity similar to those of the copper foil 60 and the electrically/thermally conductive member 61. In general, the thermal conductivity of the electrically insulating thermally conductive member 62 is lower than the thermal conductivities of the copper foil 60 and the electrically/thermally conductive member 61. In this case, if the thickness of the electrically insulating thermally conductive member 62 is larger than 3 mm, the thermal conductivity may be decreased, and if the thickness of the electrically insulating thermally conductive member 62 is larger than 3 mm, the size of the endoscopic observation portion 38 is excessively increased.

Also, the exposed portion of the electrically/thermally conductive member 61 exposed to the various endoscopic structures such as the forceps pipe of the endoscopic observation portion 38, or in the illustrated example, the electrically insulating coating member 63 that provides insulating coating on the folded back portion is not particularly limited as long as the electrically/thermally conductive member 61 and the endoscopic structure can be electrically insulated or isolated from each other like the electrically insulating thermally conductive member 62, and may use a known electrically insulating coating member. For example, a member made of resin or a member made of ceramics may be used. Alternatively, a heat-shrinkable tube, an electrically insulating thin film, electrically insulating coating, or the like, may be used.

When a body cavity is observed with the ultrasonic endoscope 12, the insertion section 22 is inserted into the body cavity and searches for an observation target region while an endoscopic optical image acquired by the endoscopic observation portion 38 is observed on the monitor 20.

Then, when the distal end part 40 arrives at the observation target region and an instruction is given to acquire an ultrasonic tomographic image, a driving control signal is input to the ultrasonic vibrators 48 from the ultrasonic processor device 14 via the coaxial cables 58, the cable wiring portion 56, and the electrode part 52 in the ultrasonic endoscope 12. When the driving control signal is input, a predetermined voltage is applied to both electrodes of the ultrasonic vibrators 48. Then, the piezoelectric bodies of the ultrasonic vibrators 48 are excited, and emit ultrasonic waves to the observation target region via the acoustic lens 66.

At this time, the ultrasonic vibrators 48 and the backing material layer 54 of the distal end part 40 generate heat. The generated heat is efficiently transmitted to the copper foil 60 that constitutes the heat release structure 70. The heat transmitted through the copper foil 60 is efficiently transmitted to the erecting base assembly 92 which is the endoscopic structure via the electrically/thermally conductive member 61 connected to the copper foil 60 and the electrically insulating thermally conductive member 62, is transmitted to the operation section 24 from the erecting base assembly 92 via the bending part 42 and the soft part 44 of the insertion section 22, and is efficiently released to the outside of the body cavity of the subject. Hence, a temperature rise of the distal end part 40 of the ultrasonic endoscope 12 is suppressed, and the ultrasonic endoscope 12 does not give a damage such as a moderate-temperature burn or the like on the body cavity surface with which the distal end part 40 comes into contact. Also, the electrically insulating thermally conductive member 62 is disposed between the electrically/thermally conductive member 61 and the erecting base assembly 92, and the electrically insulating coating member 63 is disposed between the electrically/thermally conductive member 61 and another endoscopic structure. Even if electric current leaks to the erecting base assembly 92 and/or the other endoscopic structure such as the forceps pipe, the electric current does not flow to the distal end part 40. Therefore, the ultrasonic endoscope 12 according to the present invention does not give a burden due to an electric load on the subject.

In this way, after the observation target region is irradiated with ultrasonic waves, the ultrasonic vibrators 48 receive an echo signal from the observation target region. The irradiation with the ultrasonic waves and the reception of the echo signal are repeated while the ultrasonic vibrator 48 to be driven is shifted by an electronic switch such as a multiplexer. Accordingly, scanning with ultrasonic waves is provided on the observation target region. With the ultrasonic processor device 14, an ultrasonic tomographic image is generated based on a detection signal that is output from the ultrasonic vibrators 48 using the echo signal received by the ultrasonic vibrators 48. The generated ultrasonic tomographic image is displayed on the monitor 20.

The ultrasonic endoscope according to the first embodiment of the present invention is configured as described above.

The ultrasonic endoscope according to the first embodiment of the present invention releases the heat generated from the ultrasonic vibrators 48 and the backing material layer 54 of the distal end part 40 to the erecting base assembly 92 which is the endoscopic structure via the first thermally conductive member such as the copper foil 60, the second thermally conductive member such as the electrically/thermally conductive member 61, and the electrically insulating thermally conductive member 62. However, the present invention is not limited thereto. The heat may be transmitted to another endoscopic structure, or another second thermally conductive member may be used. The endoscopic structure serving as a heat release target is not limited to various erecting base components such as the above-described erecting base assembly 92, and may be a forceps pipe line component such as the forceps pipe of the treatment tool channel 90, a distal-end-side ring component of the angle sub-assembly such as the distal end ring 43a of the angle rings 43, or another electrically conductive structural body, as long as the endoscopic structure is an electrically conductive structural body of an endoscopic structure.

Figure 12:
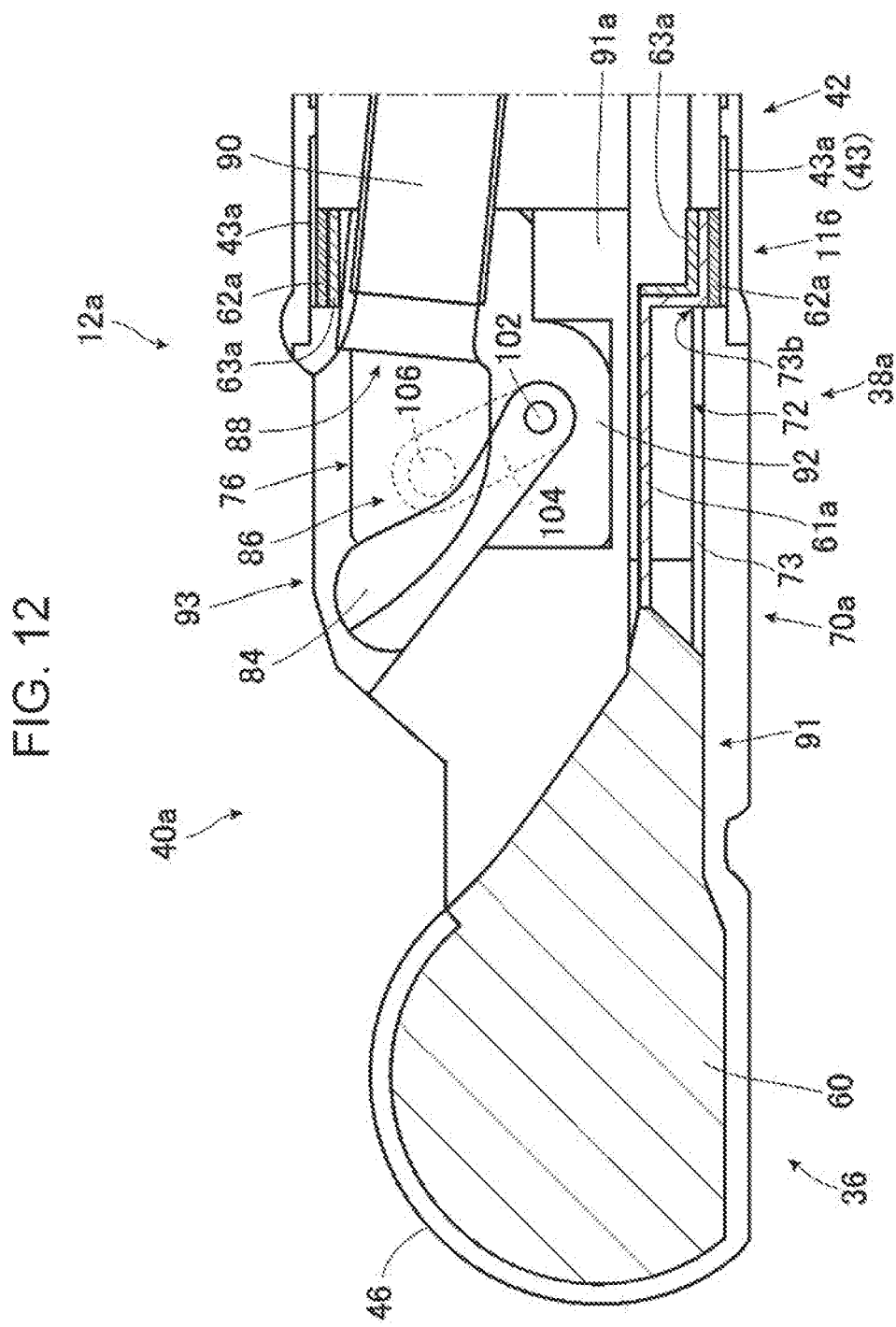
FIG. 12 is a longitudinal section schematically showing another example of a heat release structure of the distal end part of the ultrasonic endoscope shown in FIG. 4.
Figure 13:
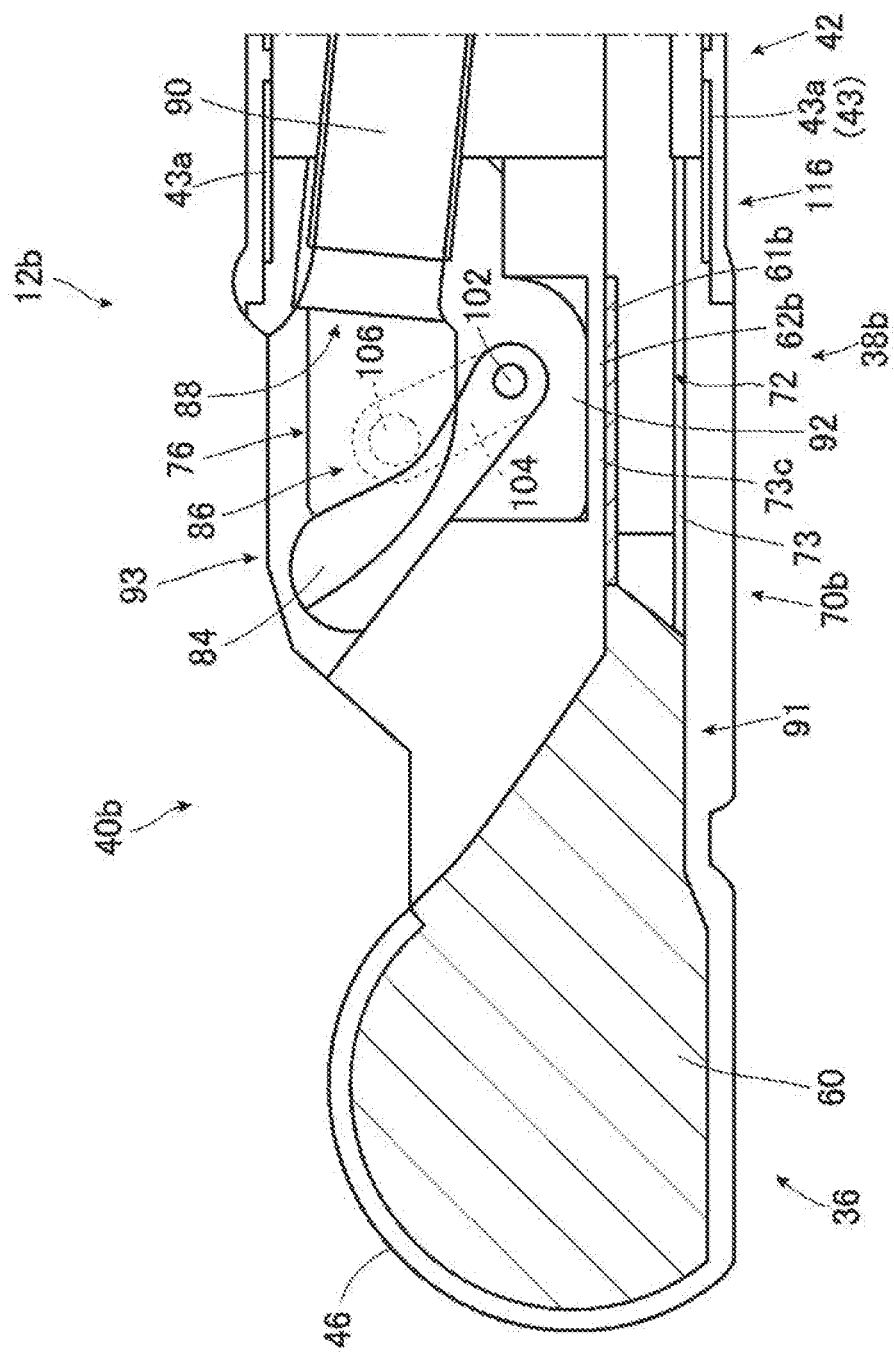
FIG. 13 is a longitudinal section schematically showing still another example of a heat release structure of the distal end part of the ultrasonic endoscope shown in FIG. 4.
Figure 14:
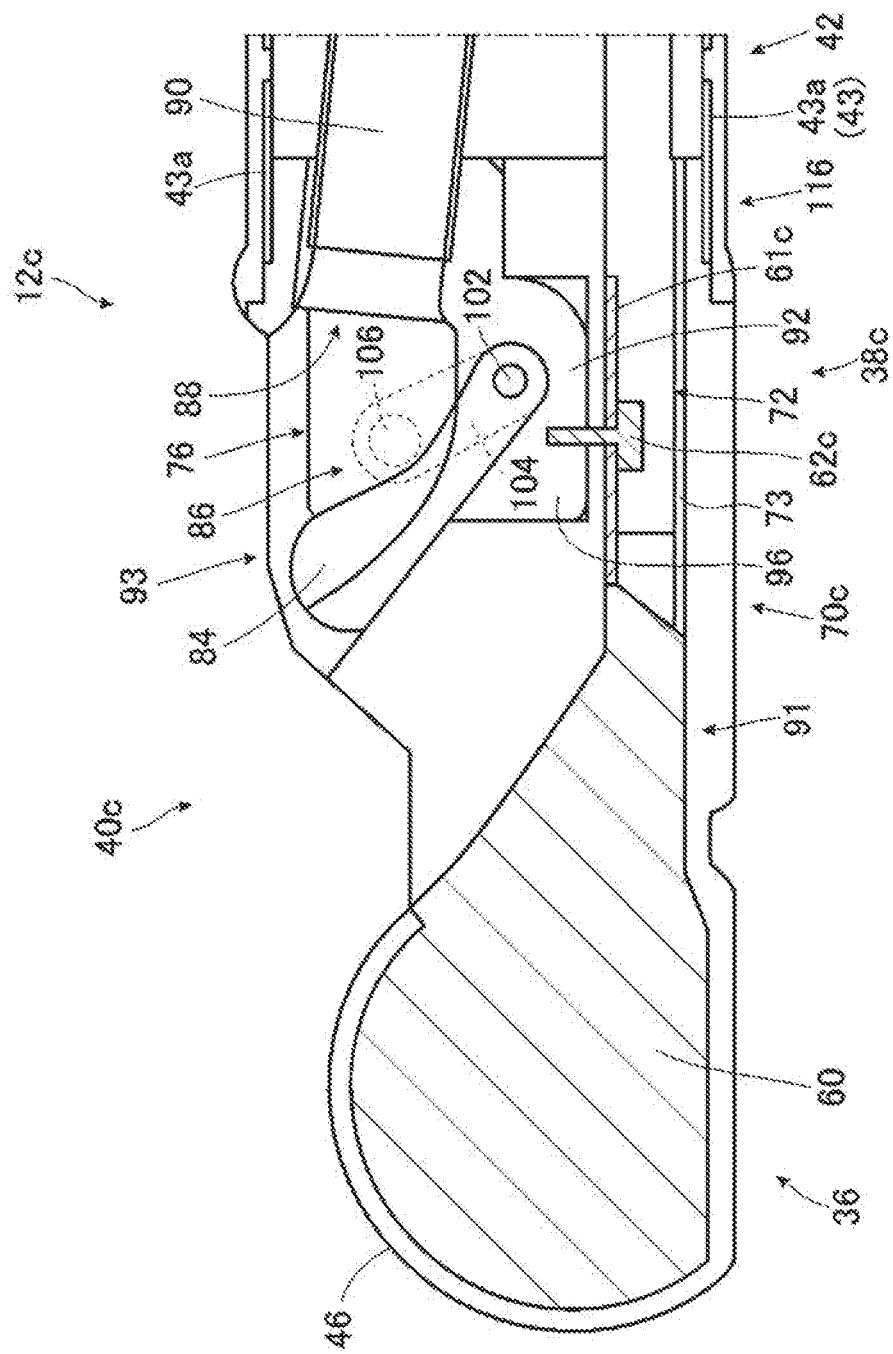
FIG. 14 is a longitudinal section schematically showing yet another example of a heat release structure of the distal end part of the ultrasonic endoscope shown in FIG. 4.

Ultrasonic endoscopes according to second to fourth embodiments of the present invention are described below with reference to FIGS. 12 to 14. FIGS. 12 to 14 are drawings that each emphasize the member and so force related to the heat release structure to explain the heat release structure of the ultrasonic endoscope according to each embodiment like FIG. 5. FIGS. 12 to 14 each emphasize the part required for the explanation, whereas simplify or omit the part not used for the explanation.

Ultrasonic observation portions of distal end parts and endoscopic observation portions of the ultrasonic endoscopes according to the second to fourth embodiments of the present invention shown in FIGS. 12 to 14 have configurations similar to those of the ultrasonic observation portion 36 including the ultrasonic vibrator unit 46 and the endoscopic observation portion 38 of the distal end part 40 of the ultrasonic endoscope 12 shown in FIG. 4, except for the heat release structure 70 shown in FIG. 5 and a modified part of the endoscopic observation portion 38 for the heat release structure 70, and has configurations similar to those of the ultrasonic endoscope 12 shown in FIGS. 1 to 4 and 6 to 11. Thus, the detailed description is omitted.

Second Embodiment

FIG. 12 is an explanatory view schematically showing a heat release structure of a distal end part of an ultrasonic endoscope according to a second embodiment of the present invention.

As shown in FIG. 12, a heat release structure 70a of a distal end part 40a of an ultrasonic endoscope 12a according to the second embodiment of the present invention includes the copper foil 60, an electrically/thermally conductive member 61a, and an electrically insulating thermally conductive member 62a. The heat release structure 70a preferably additionally includes an electrically insulating coating member 63a.

The electrically/thermally conductive member 61a thermally connects the copper foil 60 and the electrically insulating thermally conductive member 62a to each other. One end, that is, an end portion on the distal end side of the electrically/thermally conductive member 61a is connected to the copper foil 60 like the heat release structure 70 shown in FIG. 5. The other end, that is, an end portion on the proximal end side of the electrically/thermally conductive member 61a extends from the end portion on the distal end side that is the connection portion with the copper foil 60 to the proximal end side of an endoscopic observation portion 38a via the inside of the cable insertion hole 73 of the endoscopic observation portion 38a, passes through an opening 73b at a lower wall surface of the cable insertion hole 73 and is bent, extends to the inner peripheral surface on the inner side of the distal end ring 43a that is fixed to the connecting portion 116 between the endoscopic observation portion 38a and the bending part 42, and is disposed on the inner peripheral surface of the distal end ring 43a via the electrically insulating thermally conductive member 62a disposed on the inner peripheral surface of the distal end ring 43a of the angle rings 43 that are endoscopic structures.

The bent portion of the end portion on the proximal end side of the electrically/thermally conductive member 61a is open by the opening 73b of the cable insertion hole 73. Thus, the bent portion is an exposed portion exposed to other various endoscopic structures of the endoscopic observation portion 38a, such as the forceps pipe made of SUS and so forth that constitutes the treatment tool channel 90. Thus, as shown in FIG. 12, according to the present invention, the exposed portion of the electrically/thermally conductive member 61a is preferably covered with the electrically insulating coating member 63a, and is electrically insulated or isolated from the endoscopic structures such as the forceps pipe.

With the heat release structure 70a, the electrically/thermally conductive member 61a and the distal end ring 43a which is the endoscopic structure sandwich the electrically insulating thermally conductive member 62a. In this case, the electrically/thermally conductive member 61a may be pressed by a C-shaped ring-like leaf spring. Thus, the electrically insulating thermally conductive member 62 can be removably disposed on the inner peripheral surface of the distal end ring 43a, thereby improving ease of repair.

In this way, the electrically/thermally conductive member 61a is thermally connected to the distal end ring 43a but is electrically insulated or isolated from the distal end ring 43a via the electrically insulating thermally conductive member 62a. Consequently, the copper foil 60 is thermally connected to the distal end ring 43a but is electrically insulated or isolated from the distal end ring 43a via the electrically/thermally conductive member 61a and the electrically insulating thermally conductive member 62a.

Thus, the heat generated from the ultrasonic vibrators 48 and the backing material layer 54 of the distal end part 40a is transmitted to the distal end ring 43a of the angle rings 43 which are the endoscopic structures, via the first thermally conductive member such as the copper foil 60, the second thermally conductive member such as the electrically/thermally conductive member 61a, and the electrically insulating thermally conductive member 62a. As shown in FIG. 2, the heat can be further transmitted from the distal end ring 43a to the proximal end side of the plurality of angle rings 43 of the bending part 42, and can be released to the outside from the operation section 24 via the soft part 44.

Note that the electrically/thermally conductive member 61a, the electrically insulating thermally conductive member 62a, and the electrically insulating coating member 63a have similar functions and configurations as those of the electrically/thermally conductive member 61, the electrically insulating thermally conductive member 62, and the electrically insulating coating member 63 shown in FIG. 5, except for the arrangement positions and the shapes which are different due to the arrangement positions. Thus, the description is omitted.

In the example shown in FIG. 12, while the electrically insulating thermally conductive member 62a is disposed on the inner peripheral surface of the distal end ring 43a, and is sandwiched between the electrically/thermally conductive member 61a and the distal end ring 43a, the present invention is not limited thereto. The electrically insulating thermally conductive member 62a may be disposed on the outer peripheral surface on the outer side of the distal end ring 43a, and the electrically/thermally conductive member 61a may be provided on the electrically insulating thermally conductive member 62a, and hence the electrically insulating thermally conductive member 62a may be sandwiched between the electrically/thermally conductive member 61a and the distal end ring 43a. Even in this case, the electrically/thermally conductive member 61a may be pressed on a C-shaped ring-like leaf spring from the outer side, and the electrically insulating thermally conductive member 62a may be removably attached on the outer peripheral surface of the distal end ring 43a, thereby improving ease of repair.

Third Embodiment

FIG. 13 is an explanatory view schematically showing a heat release structure of a distal end part of an ultrasonic endoscope according to a third embodiment of the present invention.

As shown in FIG. 13, a heat release structure 70b of a distal end part 40b of an ultrasonic endoscope 12b according to the third embodiment of the present invention includes the copper foil 60, an electrically/thermally conductive member 61b, and an electrically insulating thermally conductive member 62b.

With the heat release structure 70b according to this embodiment, a portion with a decreased thickness of a partition wall between the cable insertion hole 73 and the bottom surface (lower surface) 96a of the base portion 96 of the erecting base assembly 92 functions as the electrically insulating thermally conductive member 62b. That is, the portion that functions as the electrically insulating thermally conductive member 62b is a wall, that is, a thin wall portion 73c, with a small thickness of the cable insertion hole 73 that contacts the bottom surface 96a of the base portion 96 of the erecting base assembly 92 that is the endoscopic structure.

The electrically/thermally conductive member 61b thermally connects the copper foil 60 and the thin wall portion 73c of the cable insertion hole 73 that serves as the electrically insulating thermally conductive member 62b to each other. One end, that is, an end portion on the distal end side of the electrically/thermally conductive member 61b is connected to the copper foil 60 like the heat release structure 70 shown in FIG. 5. The other end, that is, an end portion on the proximal end side of the electrically/thermally conductive member 61b extends from the end portion on the distal end side which is the connection portion with respect to the copper foil 60 through the cable insertion hole 73 of an endoscopic observation portion 38b to the proximal end side of the endoscopic observation portion 38b, and is connected to a thin wall portion 73c of the cable insertion hole 73.

Consequently, with the heat release structure 70b according to this embodiment, the electrically/thermally conductive member 61b and the base portion 96 of the erecting base assembly 92 which is the endoscopic structure sandwich the thin wall portion 73c that serves as the electrically insulating thermally conductive member 62b.

In this embodiment, the thickness of the wall of the thin wall portion 73c of the cable insertion hole 73 that functions as the electrically insulating thermally conductive member 62b is required to be 3 mm or smaller, and may be preferably, 1 mm or smaller.

In this way, the electrically/thermally conductive member 61b is thermally connected to the erecting base assembly 92 via the thin wall portion 73c that serves as the electrically insulating thermally conductive member 62b, but is electrically insulated or isolated from the endoscopic structure via the thin wall portion 73c that serves as the electrically insulating thermally conductive member 62b because of not being open to the endoscopic structure. Consequently, the copper foil 60 is thermally connected to the erecting base assembly 92 but is electrically insulated or isolated from the erecting base assembly 92 via the electrically/thermally conductive member 61b and the thin wall portion 73c that serves as the electrically insulating thermally conductive member 62b.

Thus, the heat generated from the ultrasonic vibrators 48 and the backing material layer 54 of the distal end part 40b is transmitted to the erecting base assembly 92 which is the endoscopic structure, via the first thermally conductive member such as the copper foil 60, the second thermally conductive member such as the electrically/thermally conductive member 61b, and the thin wall portion 73c that functions as the electrically insulating thermally conductive member 62b. Similarly to the heat release structure 70 according to the first embodiment, the heat is transmitted to the lever operating wire 110 which is the endoscopic structure shown in FIG. 10, and/or is further transmitted from the proximal end side of the plurality of angle rings 43 of the bending part 42 shown in FIG. 2 to the soft part 44, and can be released to the outside from the operation section 24.

Note that the electrically/thermally conductive member 61b has similar function and configuration as those of the electrically/thermally conductive member 61 shown in FIG. 5, except for the different arrangement position and the different shape due to the arrangement position. Thus, the description is omitted.

Fourth Embodiment

FIG. 14 is an explanatory view schematically showing a heat release structure of a distal end part of an ultrasonic endoscope according to a fourth embodiment of the present invention.

As shown in FIG. 14, a heat release structure 70c of a distal end part 40c of an ultrasonic endoscope 12c according to the fourth embodiment of the present invention includes the copper foil 60, an electrically/thermally conductive member 61c, and a ceramic screw 62c that has high thermal conductivity and hence functions as an electrically insulating thermally conductive member.

The electrically/thermally conductive member 61c thermally connects the copper foil 60 and the ceramic screw 62c to each other. One end, that is, an end portion on the distal end side of the electrically/thermally conductive member 61c is connected to the copper foil 60 like the heat release structure 70 shown in FIG. 5. The other end, that is, an end portion on the proximal end side of the electrically/thermally conductive member 61c extends from the end portion on the distal end side which is the connection portion with respect to the copper foil 60 through the cable insertion hole 73 of an endoscopic observation portion 38c to the proximal end side of the endoscopic observation portion 38c.

The electrically/thermally conductive member 61c that extends through the inside of the cable insertion hole 73 has an insertion hole through which the screw 62c is inserted. A wall of the cable insertion hole 73 has a corresponding insertion hole corresponding to the insertion hole of the electrically/thermally conductive member 61c, and the base portion 96 of the erecting base assembly 92 adjacent to the cable insertion hole 73 has a screw hole. The ceramic screw 62c is fitted into the insertion hole of the electrically/thermally conductive member 61c, passes through the corresponding insertion hole of the wall of the cable insertion hole 73, is screwed into the screw hole of the base portion 96 of the erecting base assembly 92, and is fastened. Thus, a distal end portion of the screw 62c comes into contact with the base portion 96 of the erecting base assembly 92 which is the electrically conductive structural body of the endoscopic structure.

The electrically/thermally conductive member 61c is fixed and connected to the base portion 96 of the erecting base assembly 92 by the ceramic screw 62c with the wall of the cable insertion hole 73 sandwiched therebetween. The screw 62c is removably attached to the erecting base assembly 92. Hence, the heat release structure 70c is easily repaired.

In this way, the electrically/thermally conductive member 61c is thermally connected to the erecting base assembly 92 via the ceramic screw 62c, but is not open to the endoscopic structure. Thus, the electrically/thermally conductive member 61c is electrically insulated or isolated from the endoscopic structure. Consequently, the copper foil 60 is thermally connected to the erecting base assembly 92 but is electrically insulated or isolated from the erecting base assembly 92 via the electrically/thermally conductive member 61a and the ceramic screw 62c.

Thus, the heat generated from the ultrasonic vibrators 48 and the backing material layer 54 of the distal end part 40c is transmitted to the erecting base assembly 92 which is the endoscopic structure, via the first thermally conductive member such as the copper foil 60, the second thermally conductive member such as the electrically/thermally conductive member 61c, and the ceramic screw 62c that functions as the electrically insulating thermally conductive member. Similarly to the heat release structure 70 according to the first embodiment, the heat is transmitted from the bending part 42 to the soft part 44, and can be released to the outside from the operation section 24. To improve attachment of the screw 62c, an access hole for insertion of the screw 62c may be provided in the outer peripheral surface of the proximal assembly 91, and the access hole may be closed with a seal member or a lid-shaped member after the connection with the screw.

Note that the electrically/thermally conductive member 61c, and the ceramic screw 62c that functions as the electrically insulating thermally conductive member have similar functions and configurations as those of the electrically/thermally conductive member 61 and the electrically insulating thermally conductive member 62 shown in FIG. 5 except for the arrangement positions and the shapes which are different due to the arrangement positions. Thus, the description is omitted.

While the ultrasonic endoscope including the heat release structure at the distal end part according to any one of the first to fourth embodiments of the present invention is a convex-type ultrasonic endoscope including an erecting base in a treatment tool lead-out portion of an endoscopic observation portion, the present invention is not limited thereto. A convex-type ultrasonic endoscope including a heat release structure at a distal end part having an endoscopic observation portion not including an erecting base may be employed.

Ultrasonic endoscopes according to fifth and sixth embodiments of the present invention are described below with reference to FIGS. 15 to 18.

Figure 15:
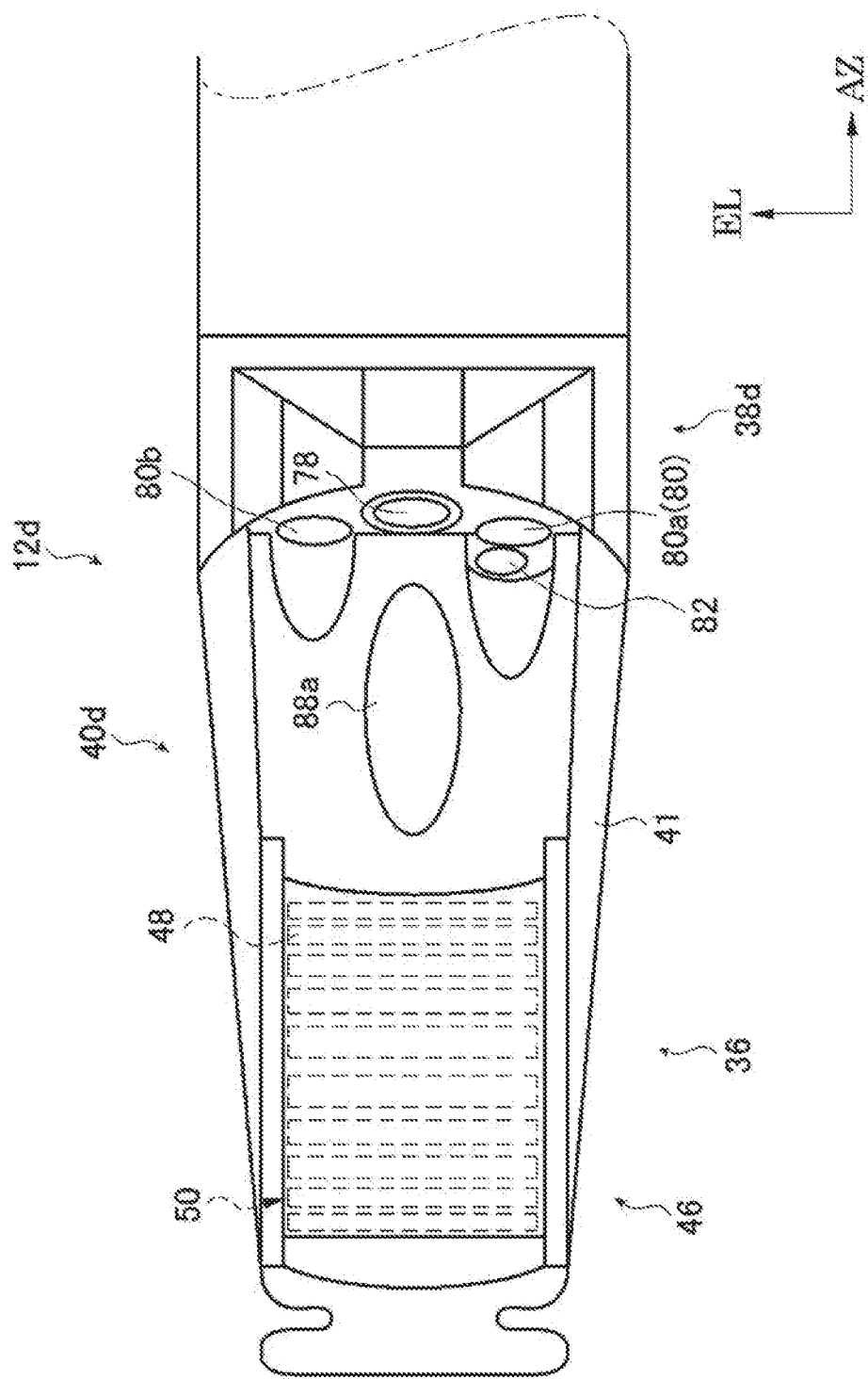
FIG. 15 is a partial enlarged plan view showing an example of a distal end part of an ultrasonic endo scope according to another embodiment of the present invention.
Figure 16:
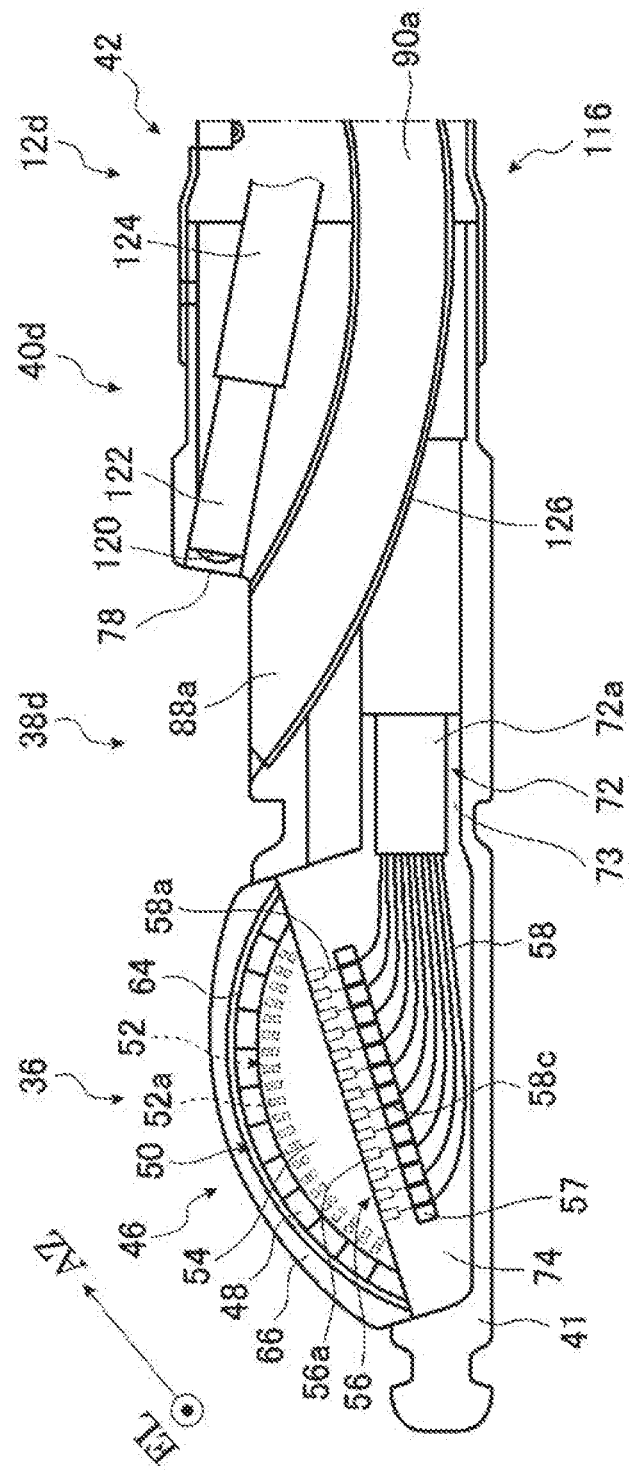
FIG. 16 is a longitudinal section schematically showing an example of the distal end part of the ultrasonic endoscope shown in FIG. 15.
Figure 17:
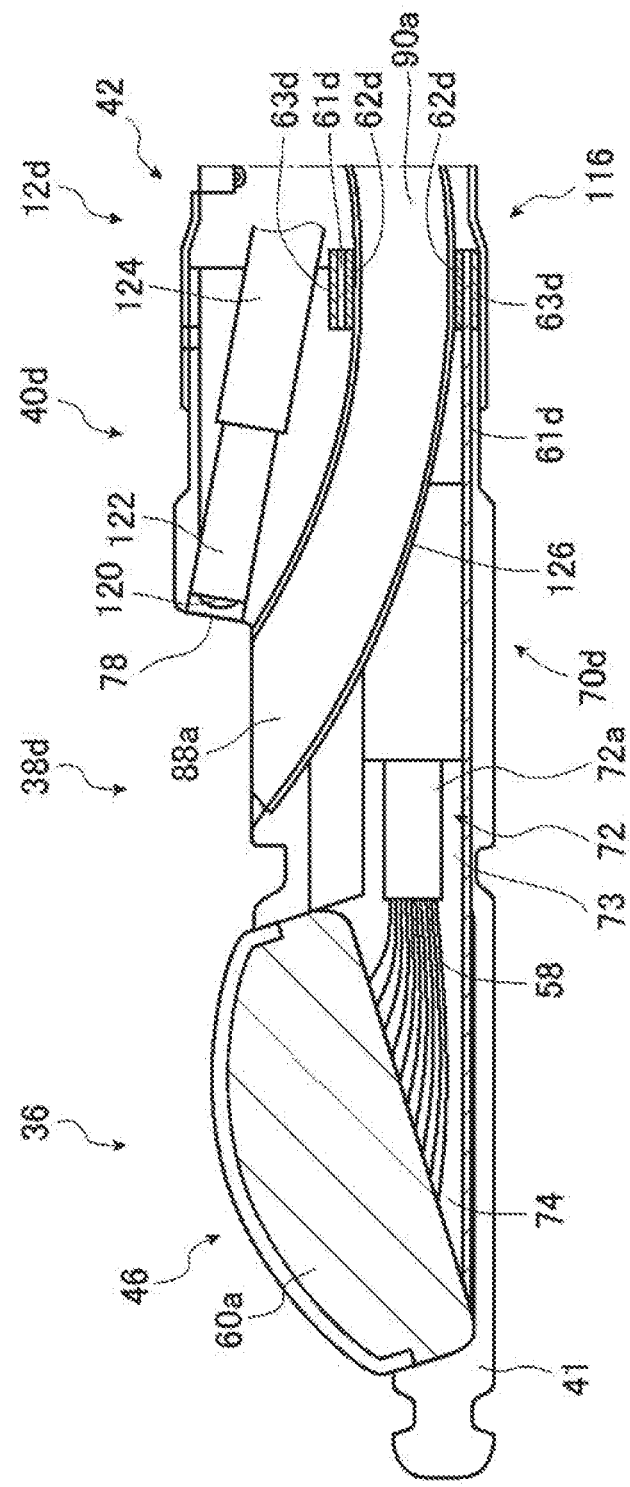
FIG. 17 is a longitudinal section schematically showing an example of a heat release structure of the distal end part of the ultrasonic endoscope shown in FIG. 15.
Figure 18:
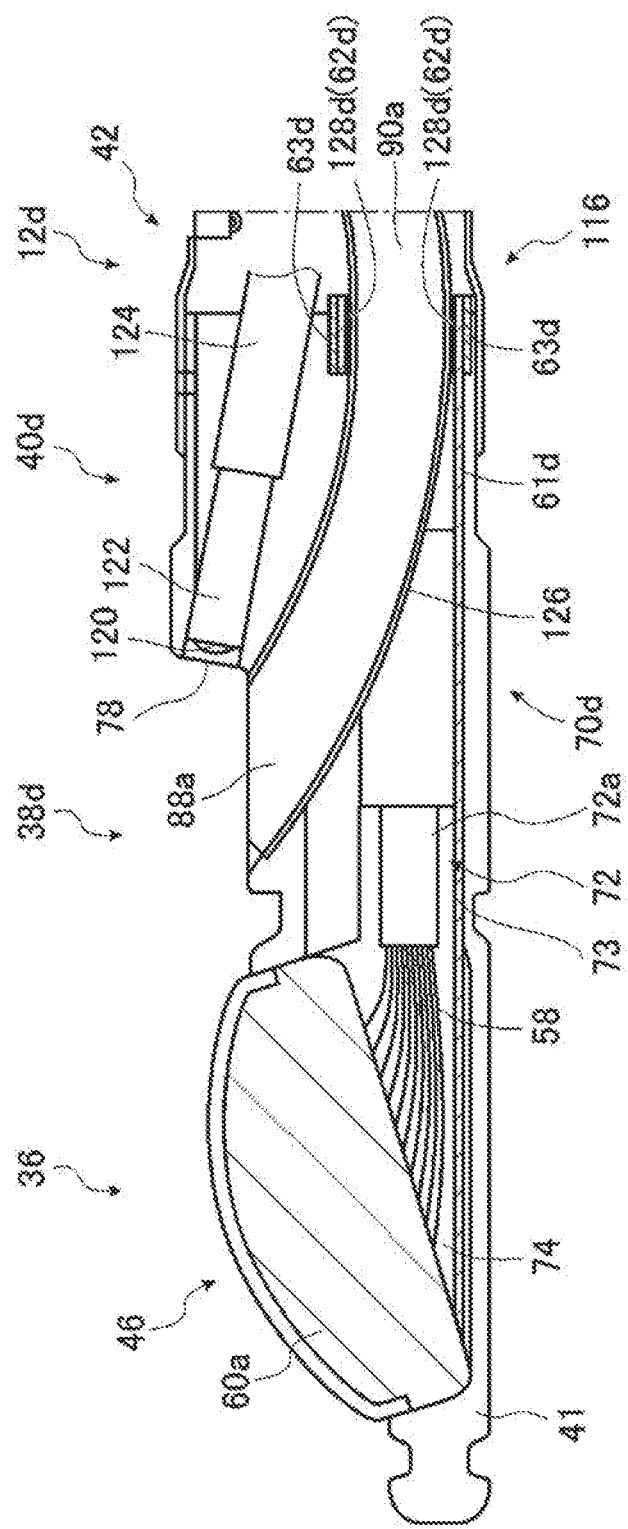
FIG. 18 is a longitudinal section schematically showing another example of a heat release structure of the distal end part of the ultrasonic endoscope shown in FIG. 15.

Ultrasonic observation portions of distal end parts and endoscopic observation portions of the ultrasonic endoscopes according to the fifth and sixth embodiments of the present invention shown in FIGS. 15 to 18 have configurations similar to those of the ultrasonic observation portion 36 including the ultrasonic vibrator unit 46 and the endoscopic observation portion 38 of the distal end part 40 of the ultrasonic endoscope 12 shown in FIG. 4 except that the endoscopic observation portion does not include the erecting base and the heat release structure 70 shown in FIG. 5 and the endoscopic observation portion 38 for the heat release structure 70 have modified portions. Also, the other configurations of the ultrasonic endoscopes according to the fifth and sixth embodiments of the present invention shown in FIGS. 15 to 18 have configurations similar to those of the ultrasonic endoscope 12 shown in FIGS. 1 to 4 and 6 to 11. Thus, the detailed description is omitted. FIGS. 16 to 18 are drawings that each emphasize the member and so force related to the heat release structure to explain the heat release structure of the ultrasonic endoscope according to each embodiment like FIG. 5. FIGS. 16 to 18 each emphasize the part required for the explanation, whereas simplify or omit the part not used for the explanation.

Fifth Embodiment

FIG. 15 is a partial enlarged plan view showing a distal end part and its periphery of an ultrasonic endoscope according to this embodiment. FIG. 16 is a schematic longitudinal section of the distal end part of the ultrasonic endoscope shown in FIG. 15 when cut along the center line in a longitudinal direction thereof. FIG. 17 is a longitudinal section schematically showing an example of a heat release structure of the distal end part of the ultrasonic endoscope shown in FIG. 15.

First, as shown in FIGS. 15 to 17, an ultrasonic endoscope 12d according to the present invention has an ultrasonic observation portion 36 including a heat release structure 70d being a feature of the present invention, and an endoscopic observation portion 38d at a distal end part 40d, image captures the inside of a body cavity of a subject, and acquires an ultrasound image and an endoscope image.

The distal end part 40d of the ultrasonic endoscope 12d shown in FIGS. 15 and 16 is provided with the ultrasonic observation portion 36 on the distal end side, the endoscopic observation portion 38d on the proximal end side, and a treatment tool lead-out port 88a therebetween. The ultrasonic observation portion 36 and the endoscopic observation portion 38d are attached to and held by an exterior member 41 made of a rigid member such as a hard resin and serving as a distal end main body of the distal end part 40d of the ultrasonic endoscope 12d.

In the example shown in FIGS. 15 to 16, a treatment tool lead-out port 88a is provided between the ultrasonic observation portion 36 and the endoscopic observation portion 38d. However, the present invention is not particularly limited to the illustrated example. The treatment tool lead-out port 88a may be provided in the endoscopic observation portion 38d or may be provided on the proximal end side (the bending part 42 side) with respect to the endoscopic observation portion 38d.

The ultrasonic observation portion 36 is composed of an ultrasonic vibrator unit 46 including an ultrasonic vibrator array 50 in which a plurality of ultrasonic vibrators 48 are arranged in an array, and the exterior member 41 to which the ultrasonic vibrator unit 46 is attached and by which the ultrasonic vibrator unit 46 is held.

As shown in FIGS. 16 and 17, the ultrasonic vibrator unit 46 includes the ultrasonic vibrator array 50 consisting of the plurality of ultrasonic vibrators 48, an electrode part 52 including a plurality of individual electrodes 52a, a cable wiring portion 56 including a plurality of connection portions 56a, a ground bar 57, and a copper foil 60a.

As shown in FIG. 17, the copper foil 60a is a thermally conductive member that is connected to the plurality of ultrasonic vibrators 48, and constitutes the heat release structure 70d according to this embodiment. The copper foil 60a is bonded to the entirety of either side surfaces or the entirety of both outer side surfaces of the plurality of ultrasonic vibrators 48 and the backing material layer 54 like the copper foil 60 shown in FIG. 5. The copper foil 60a extends to a position below the backing material layer 54 on the side opposite to the ultrasonic vibrator array 50, and extends to the endoscopic observation portion 38. The copper foil 60a shields the plurality of ultrasonic vibrators 48 and also releases the heat generated from the plurality of ultrasonic vibrators 48 and the backing material layer 54.

As shown in FIGS. 15 to 17, the endoscopic observation portion 38d is composed of, for example, the observation window 78, the illumination windows 80 (80a, 80b), the washing (air/water supply) nozzle 82, an objective lens 120 disposed inside the observation window 78, a solid-state imaging element 122, and a wiring cable 124.

Similarly to the first embodiment according to the present invention, the reflected light of an observation target region incident through the observation window 78 forms an image on an imaging surface of the solid-state imaging element 122, such as a CCD or a CMOS, with the objective lens 120. The solid-state imaging element 122 photoelectrically converts the reflected light of the observation target region, the reflected light which has been transmitted through the observation window 78 and the objective lens 120, and has formed an image on the imaging surface, into an image signal and outputs the image signal. The image signal output from the solid-state imaging element 122 is transmitted to the endoscopic processor device 16 through the universal cord 26 via wiring cables 124 extending from the insertion section 22 to the operation section 24. The endoscopic processor device 16 performs various signal processing and image processing on the transmitted image signal, and displays the processed image signal as an endoscope optical image on the monitor 20.

As shown in FIG. 17, the heat release structure 70d of the ultrasonic endoscope 12d according to the fifth embodiment of the present invention includes the copper foil 60a, an electrically/thermally conductive member 61d, and an electrically insulating thermally conductive member 62d. The heat release structure 70d preferably additionally includes an electrically insulating coating member 63d.

The electrically/thermally conductive member 61d thermally connects the copper foil 60a and the electrically insulating thermally conductive member 62d to each other. One end, that is, an end portion on the distal end side of the electrically/thermally conductive member 61d is connected to the distal end side of a portion of the copper foil 60a extending to a position below the backing material layer 54, like the heat release structure 70 shown in FIG. 5. The other end, that is, an end portion on the proximal end side of the electrically/thermally conductive member 61d extends from the end portion on the distal end side that is the connection portion with the copper foil 60a to the proximal end side of an endoscopic observation portion 38d via the cable insertion hole 73 of the endoscopic observation portion 38d, extends to an outer peripheral surface on the outer side of a forceps pipe 126 that is a forceps pipe line component being an endoscopic structure and that constitutes a treatment tool channel (forceps pipe line) 90a, and is disposed on the outer peripheral surface of the forceps pipe 126 via the electrically insulating thermally conductive member 62d disposed on the outer peripheral surface of the forceps pipe 126.

Note that the end portion on the proximal end side of the electrically/thermally conductive member 61d disposed on the outer peripheral surface of the forceps pipe 126 is an exposed portion exposed to a variety of other endoscopic structures of the endoscopic observation portion 38d. Thus, as shown in FIG. 17, according to the present invention, the exposed portion of the electrically/thermally conductive member 61d is preferably covered with the electrically insulating coating member 63d, for example, a coil tube or a heat-shrinkable tube, and is electrically insulated or isolated from the other endoscopic structures.

With the heat release structure 70d according to this embodiment, the electrically insulating thermally conductive member 62d is wound around the periphery, that is, the outer peripheral surface of the forceps pipe 126, and the electrically/thermally conductive member 61d is wound around the electrically insulating thermally conductive member 62d. Further, a coil tube, a heat-shrinkable tube, or the like, is wound around the electrically/thermally conductive member 61d in a manner sandwiching and pressing the electrically/thermally conductive member 61d. Thus, the electrically insulating thermally conductive member 62d can be removably disposed on the outer peripheral surface of the forceps pipe 126, thereby improving ease of repair.

In this way, the electrically/thermally conductive member 61d is thermally connected to the forceps pipe 126 but is electrically insulated or isolated from the forceps pipe 126 via the electrically insulating thermally conductive member 62d. Consequently, the copper foil 60a is thermally connected to the forceps pipe 126 but is electrically insulated or isolated from the forceps pipe 126 via the electrically/thermally conductive member 61d and the electrically insulating thermally conductive member 62d.

Thus, the heat generated from the ultrasonic vibrators 48 and the backing material layer 54 of the distal end part 40d is transmitted to the forceps pipe 126 which is the endoscopic structure, via the first thermally conductive member such as the copper foil 60a, the second thermally conductive member such as the electrically/thermally conductive member 61d, and the electrically insulating thermally conductive member 62d. The heat can be released to the outside from the treatment tool insertion port 30 of the operation section 24.

According to this embodiment, as shown in FIG. 18, an electrically insulating coating layer 128d formed by applying an electrically insulating coating, such as DLC coating to the outer peripheral surface of the forceps pipe 126 is preferably used as the electrically insulating thermally conductive member 62d. Note that the insulating coating layer 128d may use any member as long as the member meets the requirements as an electrically insulating thermally conductive member used for the present invention, for example, the withstand voltage, thickness, and thermal conductivity. When the electrically insulating coating layer 128d is used, the electrically/thermally conductive member 61d can be easily wound around the forceps pipe 126 covered with the electrically/thermally conductive member 61d.

Also, with the heat release structure 70d shown in FIGS. 17 and 18, while the endoscopic structure to which the heat is released by the heat release structure 70d is the forceps pipe 126, the present invention is not limited thereto. As shown in FIG. 12, the heat release target may be the distal end ring 43a of the angle ring 43 of the bending part 42 that is the endoscopic structure. In this case, the electrically/thermally conductive member 61d, the electrically insulating thermally conductive member 62d, and the electrically insulating coating member 63d of the heat release structure 70d may be disposed like the electrically/thermally conductive member 61a, the electrically insulating thermally conductive member 62a, and the electrically insulating coating member 63a of the heat release structure 70a shown in FIG. 12.

Note that the copper foil 60a, the electrically/thermally conductive member 61d, the electrically insulating thermally conductive member 62d such as the electrically insulating coating layer 128d, and the electrically insulating coating member 63d shown in FIG. 17 have similar functions and configurations as those of the copper foil 60, the electrically/thermally conductive member 61, the electrically insulating thermally conductive member 62, and the electrically insulating coating member 63 shown in FIG. 5 except for the arrangement positions and the shapes which are different due to the arrangement positions. Thus, the description is omitted.

While the ultrasonic endoscope including the heat release structure at the distal end part according to any one of the first to fifth embodiments of the present invention is a convex-type ultrasonic endoscope including a convex-type ultrasound probe, the present invention is not limited thereto. A radial-type ultrasonic endoscope having a radial-type ultrasound probe including a heat release structure at a distal end part may be employed.

Sixth Embodiment

Figure 19:
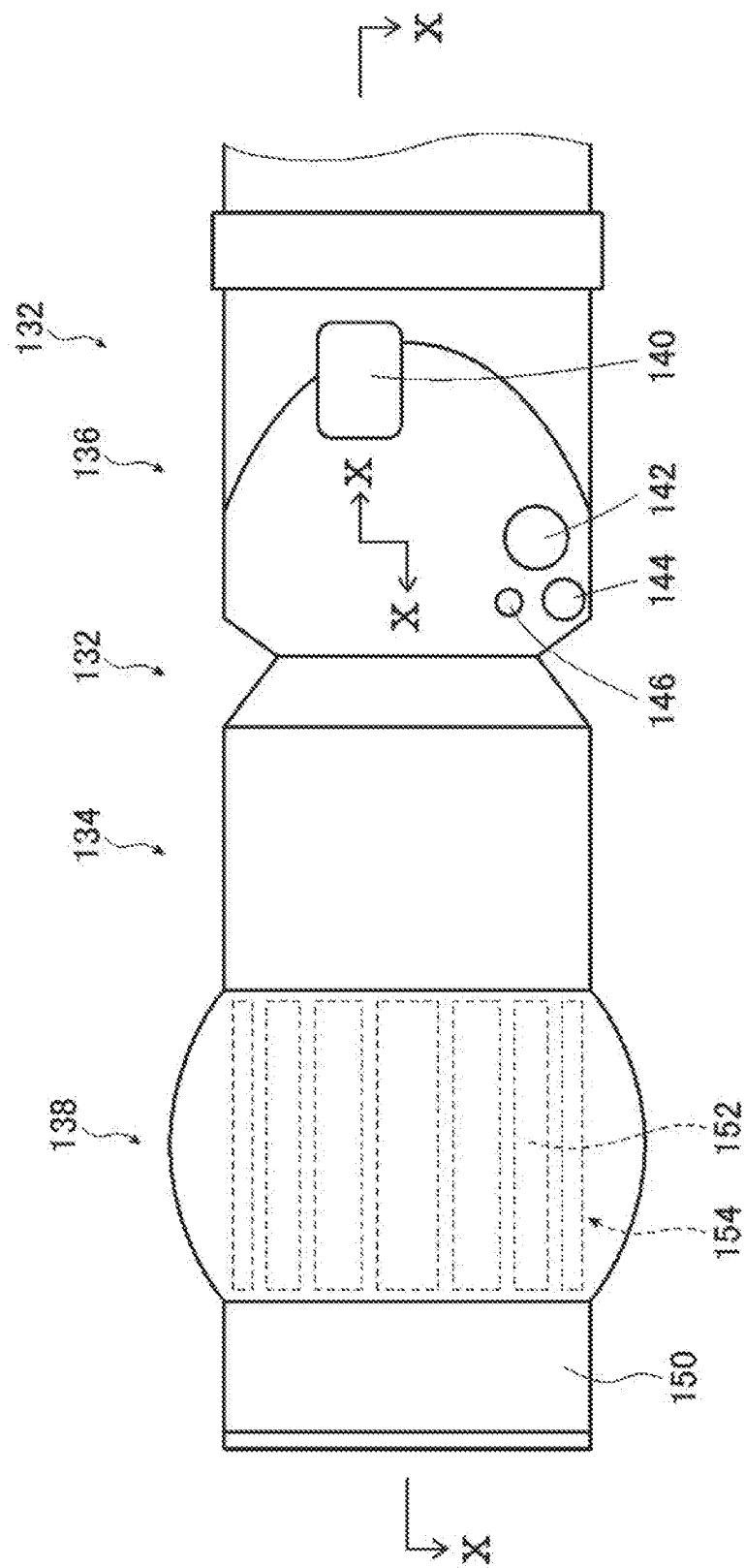
FIG. 19 is a partial enlarged plan view schematically showing a distal end part of an insertion section of an ultrasonic endoscope according to still another embodiment of the present invention.
Figure 20:
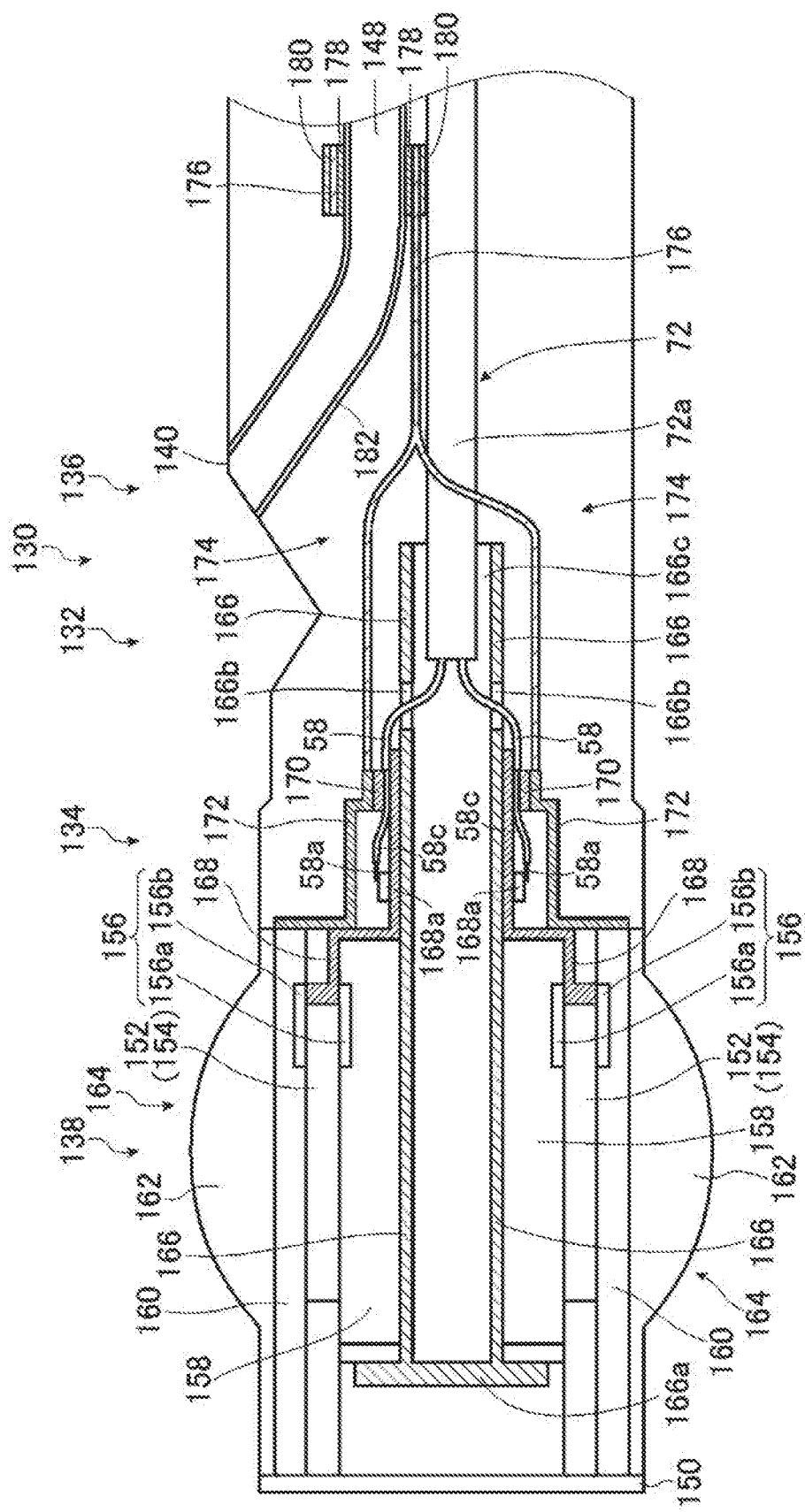
FIG. 20 is a partial longitudinal section of the distal end part of the insertion section of the ultrasonic endoscope shown in FIG. 19.

FIG. 19 is a partial enlarged plan view schematically showing a distal end part of an insertion section of an ultrasonic endoscope according to this embodiment. FIG. 20 is an arrow view taken along line XX-XX in FIG. 19, and is a partial longitudinal section of the distal end part of the insertion section of the ultrasonic endoscope shown in FIG. 19.

An ultrasonic endoscope 130 according to the sixth embodiment shown in FIGS. 19 and 20 has a configuration similar to that of the ultrasonic endoscope 12 according to the first embodiment shown in FIG. 1 except for the distal end part 40. Also, the ultrasonic endoscope 130 is similar to the ultrasonic endoscope 12d according to the fifth embodiment shown in FIGS. 15 and 16 except that the ultrasonic endoscope 130 has a distal end part 132 including a radial-type ultrasonic observation portion 134 and an endoscopic observation portion 136, instead of the distal end part 40d including the convex-type ultrasonic observation portion 36 and the endoscopic observation portion 38d. Therefore the same reference sign is applied to the same component and the redundant description is omitted.

As shown in FIGS. 19 and 20, the ultrasonic endoscope 130 according to this embodiment has the distal end part 132 of a radial-type ultrasound probe including the ultrasonic observation portion 134 and the endoscopic observation portion 136, image captures the inside of a body cavity of a subject, and acquires an ultrasound image (echo signal) and an endoscope image (image signal). The ultrasonic endoscope 130 has the insertion section (22) including the bending part (42) and the soft part (44), the operation section (24), and the universal cord (26), like the ultrasonic endoscope 12 shown in FIG. 1, in addition to the distal end part 132, although not shown in FIGS. 19 and 20.

In the example shown in FIGS. 19 and 20, while the ultrasonic observation portion 134 is disposed on the distal end side of the ultrasonic endoscope 130 with respect to the endoscopic observation portion 136, the present invention is not limited thereto. The endoscopic observation portion 136 may be located on the distal end side with respect to the ultrasonic observation portion 134, or one or some of the components of the endoscopic observation portion 136 may be located on the distal end side with respect to the ultrasonic observation portion 134.

Also, the endoscopic observation portion 136 of the ultrasonic endoscope 130 according to this embodiment has a treatment tool lead-out port (also referred to as forceps lead-out port) 140, an observation window 142, an illumination window 144, a washing nozzle 146, and so forth. Although not shown, an objective lens, a solid-state imaging element, and a wiring cable are disposed on the inner side of the observation window 142.

Note that the treatment tool lead-out port 140 is an opening through which a treatment tool is led out, and is an exit opening of a treatment tool channel (forceps pipe line) 148 that communicates with the treatment tool insertion port 30 (see FIG. 1).

With the ultrasonic endoscope 130 shown in FIGS. 19 to 20, while the treatment tool lead-out port 140 is provided in the endoscopic observation portion 136 on the proximal end side with respect to the ultrasonic observation portion 134, the present invention is not limited thereto. The treatment tool lead-out port 140 may be provided between the ultrasonic observation portion 134 and the endoscopic observation portion 136 as long as the treatment tool lead-out port 140 is located on the proximal end side with respect to the ultrasonic observation portion 134. Also, the ultrasonic endoscope 130 according to this embodiment may include a treatment tool lead-out mechanism that leads out a treatment tool such as forceps, a puncture needle, or a surgical knife through the treatment tool lead-out port 140, like the ultrasonic endoscope 12 according to the first embodiment shown in FIGS. 2 to 5, and 9 to 11.

Note that the treatment tool lead-out port 140, the observation window 142, the illumination window 144, and the washing nozzle 146; and the objective lens, the solid-state imaging element, and the wiring cable which are not shown have configurations similar to those of the treatment tool lead-out port 88a, the observation window 78, the illumination window 80, and the washing nozzle 82 shown in FIG. 16; and the objective lens 120, the solid-state imaging element 122, and the wiring cable 124 which are not shown. Therefore, the description is omitted.

As shown in FIGS. 19 and 20, the ultrasonic observation portion 134 according to this embodiment is composed of an ultrasonic vibrator unit 138, a cylindrical exterior member 150 to which the ultrasonic vibrator unit 138 is attached and by which the ultrasonic vibrator unit 138 is held, and a plurality of coaxial cables 58 of a shield cable 72 arranged in the ultrasonic vibrator unit 138.

As shown in FIG. 20, the ultrasonic vibrator unit 138 has an ultrasonic vibrator array 154 with a plurality of ultrasonic vibrators 152 arranged in a cylindrical form, an electrode part 156 having electric continuity with the ultrasonic vibrator array 154, a backing material layer 158 that supports the ultrasonic vibrators 152 of the ultrasonic vibrator array 154 from a surface on the center side of the ultrasonic vibrator unit 138 (surfaces on the inner side of the ultrasonic vibrators 152), an acoustic matching layer 160 laminated on the ultrasonic vibrator array 154 on the side opposite to the backing material layer 158 (on the outer side of the ultrasonic vibrator array 154), and an acoustic lens 162 laminated on the acoustic matching layer 160 on the side opposite to the ultrasonic vibrator array 154 (on the outer side of the acoustic matching layer 160). Thus, the ultrasonic vibrator unit 138 has a laminated body 164 consisting of the acoustic lens 162, the acoustic matching later 160, the ultrasonic vibrator array 154, and the backing material layer 158.

In this case, the electrode part 156 includes individual electrodes 156a for the plurality of ultrasonic vibrators 152 of the ultrasonic vibrator array 154, and a common electrode 156b common to the plurality of ultrasonic vibrators 152.

Also, the backing material layer 158 is supported by a cylindrical member 166 having a flange 166a and disposed on the center side. The cylindrical member 166 has at least one slit 166b that extends through the cylindrical member 166, at a position close to an end portion on the proximal end side of the laminated body 164.

Note that the ultrasonic vibrators 152, the ultrasonic vibrator array 154, the electrode part 156, the backing material layer 158, the acoustic matching layer 160, the acoustic lens 162, and the laminated body 164 according to this embodiment are formed in cylindrical shapes, and have configurations and functions similar to, although shapes are different from, those of the ultrasonic vibrators 48, the ultrasonic vibrator array 50, the electrode part 52, the backing material layer 54, the acoustic matching layer 64, the acoustic lens 66, and the laminated body 68 according to the first embodiment shown in FIGS. 1 to 4.

The ultrasonic vibrator unit 138 further includes a flexible printed circuit (FPC) 168 that is electrically connected to the plurality of individual electrodes 156a of the electrode part 156 and that includes a plurality of connection portions 168a for connection with signal lines 58a of the plurality of coaxial cables 58 through wiring, a ground bar 170 electrically connected to the common electrode 156b of the electrode part 156, and a copper foil 172 bonded to a surface of the FPC 168 on the proximal end side on the side opposite to a side end surface (an end surface on the endoscopic observation portion 136 side) of the backing material layer 158.

In this case, the FPC 168 is disposed on the side end surface (the end surface on the endoscopic observation portion 136 side) of the backing material layer 158 with the cylindrical shape. One end portion of the FPC 168 is disposed along an outer peripheral surface adjacent to the side end surface of the backing material layer 158, and is electrically connected to the plurality of individual electrodes 156a and the common electrode 156b of the electrode part 156. The other end portion of the FPC 168 extends from the side end surface of the backing material layer 158, comes into contact with the cylindrical member 166, extends along the outer peripheral surface of the cylindrical member 166, and extends to the endoscopic observation portion 136 side.

Also, the signal lines 58a of the plurality of coaxial cables 58 are individually electrically connected to the plurality of connection portions 168a of the FPC 168 electrically connected to the plurality of individual electrodes 156a of the electrode part 156. The connection portions 168a electrically connect the individual electrodes 156a of the plurality of ultrasonic vibrators 152 individually with the signal lines 58a of the plurality of coaxial cables 58.

In addition, shield members 58c of the plurality of coaxial cables 58 are sandwiched between ground wiring of the FPC 168 electrically connected to the common electrode 156b of the electrode part 156, and the ground bar 170. The shield members 58c of the plurality of coaxial cables 58 are electrically connected to the ground bar 170, and the ground wiring of the FPC 168 is electrically connected to the ground bar 170. Thus, the common electrode 156b of the plurality of ultrasonic vibrators 152 is electrically connected to the shield members 58c of the plurality of coaxial cables 58.

The plurality of coaxial cables 58, the signal lines 58a thereof, and the shield members 58c thereof pass through the at least one slit 166b of the cylindrical member 166, extend from the inside to the outside of the cylindrical member 166, and are connected to the plurality of connection portions 168a of the FPC 168, and the ground bar 170.

Note that, the plurality of coaxial cables 58, the connection portions of the signal lines 58a with the plurality of connection portions 168a of the FPC 168 of the signal lines 58a, and the connection portions of the shield members 58c of the plurality of coaxial cables 58 with the ground bar 170 are preferably filled with a filling material to avoid unbinding of the plurality of coaxial cables 58 or faulty connection of the connection portions, and thus a filling material layer (not shown) is preferably formed at the slit 166b of the cylindrical member 166 and an inner pipe line 166c near the slit 166b.

As shown in FIG. 20, a heat release structure 174 of the ultrasonic endoscope 130 according to the sixth embodiment of the present invention includes the copper foil 172, an electrically/thermally conductive member 176, and an electrically insulating thermally conductive member 178. The heat release structure 174 preferably additionally includes an electrically insulating coating member 180.

The copper foil 172 is a thermally conductive member that is thermally connected to the plurality of ultrasonic vibrators 152, and constitutes the heat release structure 174 according to this embodiment. The copper foil 172 is bonded to the ultrasonic vibrator array 154 in which the plurality of ultrasonic vibrators 152 are arranged in a cylindrical form, and a surface of the FPC 168 corresponding to the position of either side surface or the positions of both outer side surfaces of the backing material layer 158 with a cylindrical shape. The copper foil 172 is bent to the proximal end side from a position corresponding to the backing material layer 158 on the side opposite to the ultrasonic vibrator array 154, and extends to the endoscopic observation portion 136 in parallel to the center line of the cylindrical member 166. The copper foil 172 shields the plurality of ultrasonic vibrators 152 and also releases the heat generated from the plurality of ultrasonic vibrators 152 and the backing material layer 158.

In the illustrated example, the copper foil 172 is connected to the ground bar 170 connected to the shield members 58c of the plurality of coaxial cables 58, that is, to the connection portion between the shield members 58c of the plurality of coaxial cables 58 and the ground bar 170. However, the present invention is not limited thereto, and the copper foil 172 may not be connected to the ground bar 170 and the shield members 58c of the plurality of coaxial cables 58.

The electrically/thermally conductive member 176 consists of at least one member, and thermally connects the copper foil 172 and the electrically insulating thermally conductive member 178 to each other. One end, that is, an end portion on the distal end side of the electrically/thermally conductive member 176 is connected to the distal end side of a portion of the copper foil 172 extending from the position corresponding to the backing material layer 158 to the endoscopic observation portion 136, at the connection portion between the shield members 58c and the ground bar 170. The other end, that is, an end portion on the proximal end side of the electrically/thermally conductive member 176 extends from the end portion on the distal end side that is the connection portion with the copper foil 172 to the proximal end side of an endoscopic observation portion 136 via the outside of the cylindrical member 166 of the endoscopic observation portion 136 substantially in parallel to the center line thereof, extends to the outer peripheral surface on the outer side of a forceps pipe 182 that is a forceps pipe line component being an endoscopic structure and that constitutes a treatment tool channel (forceps pipe line) 148, and is disposed on the outer peripheral surface of the forceps pipe 182 via the electrically insulating thermally conductive member 178 disposed on the outer peripheral surface of the forceps pipe 182.

Note that the plurality of coaxial cables 58 including the signal lines 58a and the shield members 58c connected to the plurality of connection portions 168a of the FPC 168 and the ground bar 170 pass through the slit 166b of the cylindrical member 166 of the endoscopic observation portion 136, enter the inner pipe line 166c, are bundled as a shield cable 72 at the inner pipe line 166c, pass through the inner pipe line 166c, and are headed to the proximal end side of the endoscopic observation portion 136.

In this case, the slit 166b may be one slit 166b or a plurality of slits 166b as long as the plurality of coaxial cables 58, the signal lines 58a thereof, and the shield members 58c thereof can pass through the slit 166b.

In this case, an end portion on the proximal end side of the electrically/thermally conductive member 176 disposed on the outer peripheral surface of the forceps pipe 182 is an exposed portion exposed to a variety of other endoscopic structures of the endoscopic observation portion 136. Thus, as shown in FIG. 20, according to the present invention, the exposed portion of the electrically/thermally conductive member 176 is preferably covered with the electrically insulating coating member 180, for example, a coil tube or a heat-shrinkable tube, and is electrically insulated or isolated from the other endoscopic structures.

With the heat release structure 174 according to this embodiment, like the heat release structure 70d shown in FIGS. 17 and 18, the electrically insulating thermally conductive member 178 is wound around the periphery, that is, the outer peripheral surface of the forceps pipe 182, and the electrically/thermally conductive member 176 is wound around the electrically insulating thermally conductive member 178. Further, a coil tube, a heat-shrinkable tube, or the like, is wound around the electrically/thermally conductive member 176 in a manner sandwiching and pressing the electrically/thermally conductive member 176. Thus, the electrically insulating thermally conductive member 178 can be removably disposed on the outer peripheral surface of the forceps pipe 182, thereby improving ease of repair.

In this way, the electrically/thermally conductive member 176 is thermally connected to the forceps pipe 182 but is electrically insulated or isolated from the forceps pipe 182 via the electrically insulating thermally conductive member 178. Consequently, the copper foil 172 is thermally connected to the forceps pipe 182 but is electrically insulated or isolated from the forceps pipe 182 via the electrically/thermally conductive member 176 and the electrically insulating thermally conductive member 178.

Thus, the heat generated from the ultrasonic vibrators 152 and the backing material layer 158 of the distal end part 132 is transmitted to the forceps pipe 182 which is the endoscopic structure, via the first thermally conductive member such as the copper foil 172, the second thermally conductive member such as the electrically/thermally conductive member 176, and the electrically insulating thermally conductive member 178. The heat can be released to the outside from the treatment tool insertion port 30 of the operation section 24.

According to this embodiment, an electrically insulating coating layer formed by applying, for example, DLC coating to the outer peripheral surface of the forceps pipe 182 is preferably used as the electrically insulating thermally conductive member 178 shown in FIG. 20, like the fifth embodiment shown in FIG. 18.

Also, with the heat release structure 174 shown in FIG. 20, like the heat release structure 70d shown in FIG. 17, as shown in FIG. 12, an endoscopic structure serving as a heat release target may be the distal end ring 43a of the angle ring 43 of the bending part 42.

Note that the copper foil 172, the electrically/thermally conductive member 176, the electrically insulating thermally conductive member 178, and the electrically insulating coating member 180 shown in FIG. 20 have similar functions and configurations as those of the copper foil 60, the electrically/thermally conductive member 61, the electrically insulating thermally conductive member 62, and the electrically insulating coating member 63 shown in FIG. 5 except for the arrangement positions and the shapes which are different due to the arrangement positions. Thus, the description is omitted.

The ultrasonic endoscope according to the present invention has been described above in detail with reference to various embodiments and various examples; however, the invention is not limited to the above-described embodiments and examples, and as the matter of course the embodiments and examples may be improved and modified in various ways within the scope of the invention.

REFERENCE SIGNS LIST 10 ultrasonic inspection system
12, 12a, 12b, 12c, 12d, 130 ultrasonic endoscope
14 ultrasonic processor device
16 endoscopic processor device
18 light source device
20 monitor
21a water supply tank
21b suction pump
22 insertion section
24 operation section
26 universal cord
27 erecting operation lever
28a air/water supply button
28b suction button 29 angle knob
30 treatment tool insertion port (forceps port)
32a ultrasonic connector
32b endoscope connector
32c light source connector
34a air/water supply tube
34b suction tube
36, 134 ultrasonic observation portion
38, 38a, 38b, 38c, 38d, 136 endoscopic observation portion
40, 40a, 40b, 40c, 40d, 132 distal end part
41, 150 exterior member (distal end case)
42 bending part
43 angle ring
43a distal end ring
44 soft part
46, 138 ultrasonic vibrator unit
48, 152 ultrasonic vibrator
50, 154 ultrasonic vibrator array
52, 156 electrode part
52a, 156a individual electrode
52b, 156b common electrode
54, 158 backing material layer
56 cable wiring portion
56a, 168a connection portion
58 coaxial cable
58a signal line
58b first insulating layer
58c shield member
58d second insulating layer
57, 170 ground bar
60, 60a, 172 copper foil
61, 61a, 61b, 61c, 61d, 176 electrically/thermally conductive member
62, 62a, 62b, 62c, 62d, 178 electrically insulating thermally conductive member
63, 63a, 63d, 180 electrically insulating coating member
64, 160 acoustic matching layer
66, 162 acoustic lens
68, 164 laminated body
70, 70a, 70b, 70c, 70d, 174 heat release structure
72 shield cable
72a outer cover
73 cable insertion hole
73a, 73b opening
73c thin wall portion
74 filling material layer
76 treatment tool lead-out port
77a, 77b inclined surface
78, 142 observation window
80, 80a, 80b, 144 illumination window
82, 146 washing nozzle
84 erecting base
84a support portion
86 erecting base housing portion
88, 88a, 140 treatment tool lead-out port (forceps lead-out port)
90, 90a, 148 treatment tool channel (forceps pipe line)
91 proximal assembly
91a support portion
92 erecting base assembly
93 head assembly
94 driving mechanism portion
95 base portion
96a bottom surface (lower surface)
98 lever housing portion
98a housing space
98b side wall portion
100 treatment tool insertion portion
100a lower surface
101 treatment tool insertion hole
102 rotating shaft
104 erecting lever
104a through hole
106 columnar member
108 control cable
110 lever operating wire
112 linking member
114 forceps tube
116 connecting portion
116a intermediate diameter portion
116b small diameter portion
117a, 117b opening
118 screw hole
119 screw
120 objective lens
122 solid-state imaging element
124 wiring cable
126, 182 forceps pipe
128d electrically insulating coating layer
166 cylindrical member
166a flange
166b slit
166c inner pipe line
168 flexible printed circuit (FPC)
EL longitudinal direction (elevation direction)
AZ parallel direction (azimuth direction)

What is claimed is:

1. An ultrasonic endoscope, comprising:
a plurality of ultrasonic vibrators;
a distal end part that houses the plurality of ultrasonic vibrators;
an electrically conductive endoscopic structure housed in or connected to the distal end part;
a thermally conductive member connected to the plurality of ultrasonic vibrators; and
an electrically insulating thermally conductive member connected to the endoscopic structure,
wherein the thermally conductive member and the electrically insulating thermally conductive member are connected to each other,
wherein the thermally conductive member is an electrically/thermally conductive member,
wherein the endoscopic structure is made of metal, and
wherein heat generated from the plurality of ultrasonic vibrators is transferred to the endoscope structure via the thermally conductive member and the electrically insulating thermally conductive member, and released from the distal end part.

2. The ultrasonic endoscope according to claim 1, wherein the thermally conductive member has a first thermally conductive member that is directly connected to the plurality of ultrasonic vibrators, and a second thermally conductive member that connects the first thermally conductive member and the electrically insulating thermally conductive member to each other.

3. The ultrasonic endoscope according to claim 2,
wherein the first thermally conductive member and the second thermally conductive member are copper foil, are bonded to either surfaces, both outer side surfaces, or a rear surface side of the plurality of ultrasonic vibrators, extend to a proximal end side of the ultrasonic endoscope on the side opposite to the ultrasonic vibrators, and have their proximal end sides connected to the electrically insulating thermally conductive member.

4. The ultrasonic endoscope according to claim 1, wherein the electrically insulating thermally conductive member is removably connected to the thermally conductive member or the endoscopic structure.

5. The ultrasonic endoscope according to claim 1,
wherein the thermally conductive member has an exposed portion exposed to the endoscopic structure, and
wherein the exposed portion is covered with an electrically insulating coating member.

6. The ultrasonic endoscope according to claim 1, wherein the electrically insulating thermally conductive member has a withstand voltage of 1.5 kV or higher.

7. The ultrasonic endoscope according to claim 1, wherein the electrically insulating thermally conductive member has a thickness of 3 mm or smaller.

8. The ultrasonic endoscope according to claim 1, wherein the electrically insulating thermally conductive member has a thermal conductivity of 0.5 W/mK or higher.

9. The ultrasonic endoscope according to claim 1, wherein the endoscopic structure is an erecting base component, a forceps pipe line component, or a distal-end-side ring component of an angle sub-assembly.

10. The ultrasonic endoscope according to claim 9, wherein at least one of the erecting base component or the forceps pipe line component is disposed on a proximal end side of the ultrasonic endoscope with respect to the plurality of ultrasonic vibrators.

11. The ultrasonic endoscope according to claim 1, wherein the thermally conductive member has a thermal conductivity of 0.5 W/mK or higher.

12. The ultrasonic endoscope according to claim 1, further comprising:
a plurality of ultrasonic cables individually connected to the plurality of ultrasonic vibrators; and
a cable insertion hole that are provided in the distal end part and through which the plurality of ultrasonic cables are inserted,
wherein the thermally conductive member is partly disposed in the cable insertion hole.

13. The ultrasonic endoscope according to claim 12,
wherein the thermally conductive member has a first thermally conductive member that is directly connected to the plurality of ultrasonic vibrators, and a second thermally conductive member that connects the first thermally conductive member and the electrically insulating thermally conductive member to each other, and
wherein the second thermally conductive member is disposed in the cable insertion hole.

14. The ultrasonic endoscope according to claim 12,
wherein the electrically insulating thermally conductive member is a wall of the cable insertion hole that contacts an electrically conductive structural body of the endoscopic structure, and
wherein the wall has a thickness of 3 mm or smaller.

15. The ultrasonic endoscope according to claim 12,
wherein the plurality of ultrasonic cables are covered with an outer cover at the outermost layer and used as a single shield cable, and
wherein the single shield cable and a part of the thermally conductive member are disposed in the cable insertion hole.

16. The ultrasonic endoscope according to claim 1,
wherein the electrically insulating thermally conductive member is a thermally conductive ceramic screw that attaches the thermally conductive member to an electrically conductive structural body of the endoscopic structure, and
wherein a distal end portion of the screw contacts the electrically conductive structural body.

17. The ultrasonic endoscope according to claim 1,
wherein the distal end part has an electrically insulating exterior member, and
wherein the endoscopic structure is housed in or connected to the exterior member.

18. The ultrasonic endoscope according to claim 1, wherein the plurality of ultrasonic vibrators are convex type or radial type.

19. An ultrasonic endoscope, comprising
a plurality of ultrasonic vibrators; and
a distal end part that houses the plurality of ultrasonic vibrators,
wherein the distal end part has
an ultrasonic vibrator array in which the plurality of ultrasonic vibrators are arranged,
a distal end case that is provided on a distal end side of the ultrasonic endoscope and that houses the ultrasonic vibrator array,
a cable insertion hole that is provided in the distal end case, and through which a plurality of cables are inserted, the plurality of cables being individually electrically connected to the plurality of ultrasonic vibrators of the ultrasonic vibrator array,
an electrically conductive endoscopic structure housed in or connected to the distal end case on a proximal end side of the ultrasonic endoscope,
an electrically/thermally conductive member that is connected to the ultrasonic vibrator array and that releases heat generated from the plurality of ultrasonic vibrators, and
an electrically insulating thermally conductive member disposed in contact with the electrically conductive endoscopic structure,
wherein the electrically/thermally conductive member is extended to the proximal end side of the ultrasonic endoscope,
wherein a proximal end side of the extended electrically/thermally conductive member is connected to the electrically insulating thermally conductive member, and
wherein heat generated from the plurality of ultrasonic vibrators is transferred to the endoscope structure via the thermally conductive member and the electrically insulating thermally conductive member, and released from the distal end part.

20. An ultrasonic endoscope, comprising:
a plurality of ultrasonic vibrators; and
a distal end part that houses the plurality of ultrasonic vibrators,
wherein the distal end part has
an ultrasonic vibrator array in which the plurality of ultrasonic vibrators are arranged,
a distal end case that is provided on a distal end side of the ultrasonic endoscope and that houses the ultrasonic vibrator array,
a cable insertion hole that is provided in the distal end case, and through which a plurality of cables are inserted, the plurality of cables being individually electrically connected to the plurality of ultrasonic vibrators of the ultrasonic vibrator array,
an electrically conductive endoscopic structure housed in or connected to the distal end case on a proximal end side of the ultrasonic endoscope, an electrically conductive first thermally conductive member that is connected to the ultrasonic vibrator array and that releases heat generated from the plurality of ultrasonic vibrators, an electrically insulating thermally conductive member disposed in contact with the electrically conductive endoscopic structure, and an electrically conductive second thermally conductive member whose distal end side is connected to the first thermally conductive member, that is disposed to extend in the distal end case to the proximal end side of the ultrasonic endoscope, and whose proximal end side is connected to the electrically insulating thermally conductive member, wherein heat generated from the plurality of ultrasonic vibrators is transferred to the endoscope structure via the first thermally conductive member, the second thermally conductive member, and the electrically insulating thermally conductive member, and released from the distal end part.

* * * * *